US010244972B2

(12) United States Patent
Tominaga

(10) Patent No.: US 10,244,972 B2
(45) Date of Patent: Apr. 2, 2019

(54) FLUORESCENCE OBSERVATION DEVICE, ENDOSCOPIC SYSTEM, PROCESSOR DEVICE, AND OPERATION METHOD

(71) Applicant: FUJIFILM Corporation, Tokyo (JP)

(72) Inventor: Shunsuke Tominaga, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 568 days.

(21) Appl. No.: 15/041,553

(22) Filed: Feb. 11, 2016

(65) Prior Publication Data
US 2016/0157763 A1 Jun. 9, 2016

Related U.S. Application Data

(63) Continuation of application No. PCT/JP2014/066132, filed on Jun. 18, 2014.

(30) Foreign Application Priority Data

Sep. 27, 2013 (JP) ................................. 2013-202548

(51) Int. Cl.
*A61B 5/00* (2006.01)
*A61B 5/1455* (2006.01)
(Continued)

(52) U.S. Cl.
CPC ...... *A61B 5/14556* (2013.01); *A61B 1/00009* (2013.01); *A61B 1/043* (2013.01);
(Continued)

(58) Field of Classification Search
CPC ..... A61B 5/0066; A61B 5/0071; A61B 5/145; A61B 1/043; A61B 5/14539;
(Continued)

(56) References Cited

U.S. PATENT DOCUMENTS 5,512,940 A * 4/1996 Takasugi ............... G06T 7/0012
348/30
2002/0168096 A1* 11/2002 Hakamata ................ G06T 5/50
382/132
(Continued)

FOREIGN PATENT DOCUMENTS

| EP | 2365336 A1 | 9/2011 |
| EP | 2505140 A1 | 10/2012 |

(Continued)

OTHER PUBLICATIONS

International Preliminary Report on Patentability for PCT/JP2014/066132 (PCT/IB/373) dated Sep. 9, 2014.
(Continued)

*Primary Examiner* — Jonathan Cwern
(74) *Attorney, Agent, or Firm* — Birch, Stewart, Kolasch & Birch, LLP

(57) ABSTRACT

A fluorescence observation device includes an oxygen saturation calculation section, a reference region setting section, a region-of-interest setting section, a normalized fluorescence intensity calculation section, and a fluorescent image generation section. The oxygen saturation calculation section calculates the oxygen saturation of the subject for each pixel. The reference region setting section sets a reference region of the subject based on the oxygen saturation. The region-of-interest setting section sets a region of interest of the subject. The normalized fluorescence intensity calculation section calculates a normalized fluorescence intensity indicating the normalized emission intensity of the fluorescence by dividing the region-of-interest fluorescence intensity, which is calculated using the pixel value of the region of interest, by the reference fluorescence intensity calculated using the pixel value of the reference region of a fluorescent image signal obtained by imaging the subject with the
(Continued)

fluorescence. The fluorescent image generation section generates a fluorescent image based on the normalized fluorescence intensity.

20 Claims, 24 Drawing Sheets

(51) Int. Cl.
*A61B 1/04* (2006.01)
*A61B 1/06* (2006.01)
*A61B 5/145* (2006.01)
*A61B 1/00* (2006.01)

(52) U.S. Cl.
CPC .......... *A61B 1/0638* (2013.01); *A61B 1/0646* (2013.01); *A61B 5/14546* (2013.01); *A61B 1/00188* (2013.01); *A61B 5/14539* (2013.01); *A61B 5/7425* (2013.01)

(58) Field of Classification Search
CPC ............ A61B 5/14556; A61B 5/02007; A61B 5/0084; A61B 5/6852; A61B 2576/02; A61B 2034/20255; G06T 7/0012; G06T 2207/30052; A61F 2/82
See application file for complete search history.

(56) References Cited

U.S. PATENT DOCUMENTS

| 2009/0236541 | A1 | 9/2009 | Lomnes et al. |
| 2010/0049058 | A1 | 2/2010 | Ishihara |
| 2012/0157775 | A1* | 6/2012 | Yamaguchi .......... A61B 1/0638 600/180 |
| 2012/0253157 | A1 | 10/2012 | Yamaguchi et al. |
| 2012/0292530 | A1 | 11/2012 | Ono et al. |
| 2014/0184790 | A1 | 7/2014 | Ishihara |

FOREIGN PATENT DOCUMENTS

| JP | 2012-213550 A1 | 11/2012 |
| WO | WO 2011/099425 A1 | 8/2011 |
| WO | WO 2013/035450 A1 | 3/2013 |

OTHER PUBLICATIONS

Written Opinion of the International Searching Authority for PCT/JP2014/066132 (PCT/ISA/237) dated Sep. 9, 2014.
International Search Report for PCT/JP2014/066132 (PCT/ISA/210) dated Sep. 9, 2014.
European Office Action issued in corresponding European Application No. 14847313.5 dated Jan. 4, 2018.

* cited by examiner

FLUORESCENCE OBSERVATION DEVICE, ENDOSCOPIC SYSTEM, PROCESSOR DEVICE, AND OPERATION METHOD

CROSS-REFERENCE TO RELATED APPLICATIONS

This application is a Continuation of PCT International Application No. PCT/JP2014/066132 filed on Jun. 18, 2014, which claims priority under 35 U.S.C § 119(a) to Japanese Patent Application No. 2013-202548 filed on Sep. 27, 2013. Each of the above application(s) is hereby expressly incorporated by reference, in its entirety, into the present application.

BACKGROUND OF THE INVENTION

1. Field of the Invention

The present invention relates to a fluorescence observation device for observing a subject using fluorescence, an endoscopic system, a processor device, and an operation method.

2. Description of the Related Art

In the medical field, a fluorescence observation device that includes an excitation light source that irradiates a subject with excitation light for emitting fluorescence by exciting an auto-fluorescent material contained in the subject or a fluorescent agent administered to the subject, an image sensor that images the subject with the fluorescence emitted from the auto-fluorescent material or the fluorescent agent, and an image processing device that generates a fluorescent image, which reflects the intensity distribution of the fluorescence emitted from the subject, based on an image signal by the fluorescence output from the image sensor (hereinafter, referred to as a fluorescent image signal) is known. Since the intensity of the fluorescence emitted from the auto-fluorescent material or the fluorescent agent is closely related to the medical condition of the subject, the therapeutic effect of drugs, and the like, the fluorescence observation device is used for, for example, pathological diagnosis or drug development. In addition, in order to perform real-time diagnosis based on a fluorescent image, an endoscopic system configured to include a light source device, an endoscope, a processor device, and the like may have the configuration of the fluorescence observation device (WO2011/099425A and WO2013/035450A).

In recent years, diagnosis using the oxygen saturation of blood hemoglobin has been performed. The oxygen saturation of blood hemoglobin is calculated based on the reflection intensity, for example, by irradiating the subject with light (hereinafter, referred to as signal light) in a wavelength band where the absorption coefficients of oxygenated hemoglobin and reduced hemoglobin are different (JP2012-213550A).

SUMMARY OF THE INVENTION

Although there is a certain correlation between the fluorescence emitted from an auto-fluorescent material or a fluorescent agent and a medical condition and the like, the emission intensity changes with a subject. That is, the emission intensity of the fluorescence is greatly affected by individual differences of the subject. Accordingly, in case of fluorescence observation, there is a problem that quantitative diagnosis is difficult. For example, in WO2013/035450A, a region where there is a lesion or the like (hereinafter, referred to as a region of interest) is extracted based on the fluorescence intensity, but the region of interest may not be able to be specified correctly since there is an individual difference in the fluorescence intensity.

In WO2011/099425A, in order to eliminate the influence of such individual differences, standard data indicating the correspondence relationship between the fluorescence intensity and the medical condition of the subject is prepared in advance, and the medical condition of the subject is determined by comparison with the standard data. Thus, if the standard data is used, the accuracy of the designation of a region of interest or diagnosis may be improved in a subject with a relatively small difference from the standard data. However, in a subject with a relatively large difference from the standard data, it is not possible to eliminate the influence of the individual differences. Accordingly, a possibility of false diagnosis is high. That is, in the comparison with the standard data, it is not possible to eliminate the influence of the individual differences of the subject on the diagnosis.

It is an object of the present invention to provide a fluorescence observation device, an endoscopic system, a processor device, and an operation method capable of performing quantitative diagnosis or the like regardless of individual differences of the subject.

A fluorescence observation device of the present invention includes a signal light source, an excitation light source, an image sensor, an oxygen saturation calculation unit, a reference region setting unit, a region-of-interest setting unit, a normalized fluorescence intensity calculation unit, and a fluorescent image generation unit. The signal light source irradiates a subject with signal light having a wavelength band where an absorption coefficient changes with an oxygen saturation of blood hemoglobin. The excitation light source irradiates the subject with excitation light for emitting fluorescence by exciting a fluorescent material contained in the subject. The image sensor images the subject with the signal light and outputs a first image signal, and images the subject with the fluorescence and outputs a second image signal. The oxygen saturation calculation unit calculates an oxygen saturation of the subject for each pixel based on the first image signal. The reference region setting unit sets a reference region of the subject based on the oxygen saturation. The region-of-interest setting unit sets a region of interest of the subject. The normalized fluorescence intensity calculation unit calculates a normalized fluorescence intensity indicating a normalized emission intensity of the fluorescence by dividing a region-of-interest fluorescence intensity, which is calculated using a pixel value of the region of interest of the second image signal, by a reference fluorescence intensity calculated using a pixel value of the reference region of the second image signal. The fluorescent image generation unit generates a fluorescent image by pseudo-coloring the region of interest based on the normalized fluorescence intensity.

The region-of-interest setting unit sets the region of interest based on the oxygen saturation, for example. The region-of-interest setting unit may set the region of interest based on shape information of the subject. In addition, the reference region setting unit sets, for example, a region where the oxygen saturation falls within a specific range as the reference region.

It is preferable to include a display unit that displays a plurality of the fluorescent images, which are obtained by imaging the same subject at two or more different times, in time series.

In the case of imaging the same subject at two or more different times, it is preferable that the normalized fluorescence intensity calculation unit calculates the normalized fluorescence intensity using the region of interest set at the time of imaging at a specific time and the reference region set at the time of each imaging.

Another fluorescence observation device of the present invention includes an illumination light source, an excitation light source, an image sensor, a reference region setting unit, a region-of-interest setting unit, a normalized fluorescence intensity calculation unit, and a fluorescent image generation unit. The illumination light source irradiates a subject, at least a part of which is colored with a colorant, with illumination light by which a color due to the colorant can be identified. The excitation light source irradiates the subject with excitation light for generating fluorescence by exciting a fluorescent material contained in the subject. The image sensor images the subject with the illumination light and outputs a first image signal, and images the subject with the fluorescence and outputs a second image signal. The reference region setting unit sets a reference region according to a color due to the colorant. The region-of-interest setting unit sets a region of interest of the subject. The normalized fluorescence intensity calculation unit calculates a normalized fluorescence intensity indicating a normalized emission intensity of the fluorescence by dividing a region-of-interest fluorescence intensity, which is calculated using a pixel value of the region of interest of the second image signal, by a reference fluorescence intensity calculated using a pixel value of the reference region of the second image signal. The fluorescent image generation unit generates a fluorescent image by pseudo-coloring the region of interest based on the normalized fluorescence intensity.

The region-of-interest setting unit sets a region of interest according to a color due to the colorant. The colorant is, for example, a pH indicator that changes with pH of the subject. In the case of using the pH indicator as a colorant, the reference region setting unit sets a region where the pH is equal to or greater than a specific value as the reference region.

In addition, it is possible to use a colorant that contains at least one of indigo carmine, toluidine blue, methylene blue, Lugol's solution, crystal violet, fluorescein, acridine orange, indocyanine green, or acetic acid.

The image sensor may image the subject with the fluorescence before the colorant is administered to the subject and output the second image signal, and image the subject with the illumination light after the colorant is administered to the subject and output the first image signal.

An endoscopic system of the present invention includes a signal light source, an excitation light source, an image sensor, an oxygen saturation calculation unit, a reference region setting unit, a region-of-interest setting unit, a normalized fluorescence intensity calculation unit, and a fluorescent image generation unit. The signal light source irradiates a subject with signal light having a wavelength band where an absorption coefficient changes with an oxygen saturation of blood hemoglobin. The excitation light source irradiates the subject with excitation light for emitting fluorescence by exciting a fluorescent material contained in the subject. The image sensor images the subject with the signal light and outputs a first image signal, and images the subject with the fluorescence and outputs a second image signal. The oxygen saturation calculation unit calculates an oxygen saturation of the subject for each pixel based on the first image signal. The reference region setting unit sets a reference region of the subject based on the oxygen saturation. The region-of-interest setting unit sets a region of interest of the subject. The normalized fluorescence intensity calculation unit calculates a normalized fluorescence intensity indicating a normalized emission intensity of the fluorescence by dividing a region-of-interest fluorescence intensity, which is calculated using a pixel value of the region of interest of the second image signal, by a reference fluorescence intensity calculated using a pixel value of the reference region of the second image signal. The fluorescent image generation unit generates a fluorescent image by pseudo-coloring the region of interest based on the normalized fluorescence intensity.

A processor device of the present invention is a processor device of an endoscopic system including a signal light source, an excitation light source, and an image sensor, and includes an oxygen saturation calculation unit, a reference region setting unit, a region-of-interest setting unit, a normalized fluorescence intensity calculation unit, and a fluorescent image generation unit. The signal light source irradiates a subject with signal light having a wavelength band where an absorption coefficient changes with an oxygen saturation of blood hemoglobin. The excitation light source irradiates the subject with excitation light for emitting fluorescence by exciting a fluorescent material contained in the subject. The image sensor images the subject with the signal light and outputs a first image signal, and images the subject with the fluorescence and outputs a second image signal. The oxygen saturation calculation unit calculates an oxygen saturation of the subject for each pixel based on the first image signal. The reference region setting unit sets a reference region of the subject based on the oxygen saturation. The region-of-interest setting unit sets a region of interest of the subject. The normalized fluorescence intensity calculation unit calculates a normalized fluorescence intensity indicating a normalized emission intensity of the fluorescence by dividing a region-of-interest fluorescence intensity, which is calculated using a pixel value of the region of interest of the second image signal, by a reference fluorescence intensity calculated using a pixel value of the reference region of the second image signal. The fluorescent image generation unit generates a fluorescent image by pseudo-coloring the region of interest based on the normalized fluorescence intensity.

An operation method of the present invention is an operation method of a device including a signal light source, an excitation light source, and an image sensor, and includes an oxygen saturation calculation step, a reference region setting step, a region-of-interest setting step, a normalized fluorescence intensity calculation step, and a fluorescent image generation step. The signal light source irradiates a subject with signal light having a wavelength band where an absorption coefficient changes with an oxygen saturation of blood hemoglobin. The excitation light source irradiates the subject with excitation light for emitting fluorescence by exciting a fluorescent material contained in the subject. The image sensor images the subject with the signal light and outputs a first image signal, and images the subject with the fluorescence and outputs a second image signal. In the oxygen saturation calculation step, an oxygen saturation of the subject is calculated for each pixel based on the first image signal. In the reference region setting step, a reference region of the subject is set based on the oxygen saturation. In the region-of-interest setting step, a region of interest of the subject is set. In the normalized fluorescence intensity calculation step, a normalized fluorescence intensity indicating a normalized emission intensity of the fluorescence is calculated by dividing a region-of-interest fluorescence intensity, which is calculated using a pixel value of the region of interest of the second image signal, by a reference fluorescence intensity calculated using a pixel value of the reference region of the second image signal. In the fluorescent image generation step, a fluorescent image is generated by pseudo-coloring the region of interest based on the normalized fluorescence intensity.

According to the fluorescence observation device, the endoscopic system, the processor device, and the operation method of the present invention, it is possible to perform quantitative diagnosis or the like regardless of individual differences of the subject.

DESCRIPTION OF THE PREFERRED EMBODIMENTS

First Embodiment

Figure 1:
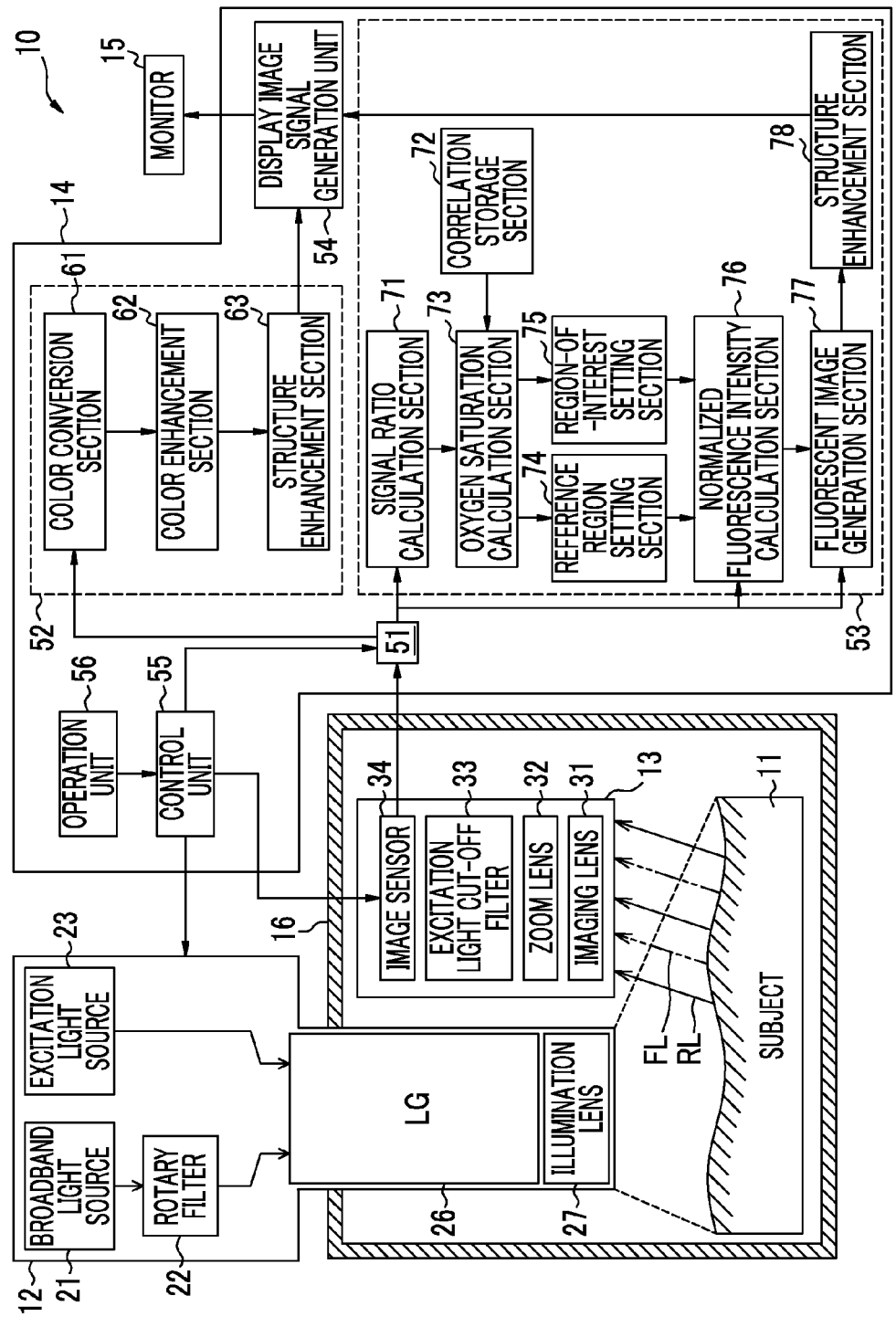
FIG. 1 is a block diagram of a fluorescence observation device.

As shown in FIG. 1, a fluorescence observation device 10 is a device for observing a subject 11 using fluorescence, and includes a light source unit 12, an imaging unit 13, a processor unit 14, and a monitor 15. The subject 11 is the entire body of a person, a mouse, or the like or a part thereof (specimens, cells, or the like cut out from an animal), and is disposed in a dark box 16 for blocking the external light.

The light source unit 12 includes a broadband light source 21, a rotary filter 22, and an excitation light source 23. The broadband light source 21 is, for example, a halogen lamp, such as a xenon lamp, or an LED, such as a white LED, and emits white light having a wavelength band ranging from blue to red. The white light emitted from the broadband light source 21 is transmitted through the rotary filter 22. Then, the white light is incident on a light guide (LG) 26 through optical members (neither is shown), such as a condensing lens, an optical fiber, and a multiplexer, is guided into the dark box 16, and is uniformly emitted to the subject 11 through an illumination lens 27.

Figure 2:
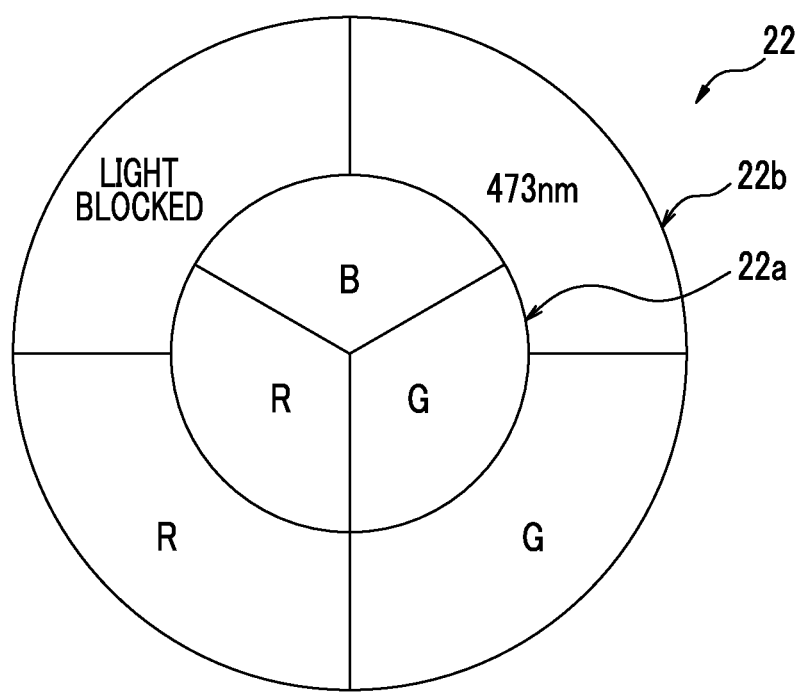
FIG. 2 is an explanatory diagram showing a rotary filter.

The rotary filter 22 is provided on the optical path of the white light that is incident on the light guide 26 from the broadband light source 21, and rotates in synchronization with the frame rate of the imaging of an image sensor 34. As observation modes, the fluorescence observation device 10 has two observation modes of a normal observation mode for observing the subject 11 in a normal color image and a special observation mode for observing the subject 11 using a fluorescent image generated based on the emission intensity of fluorescence. As shown in FIG. 2, the rotary filter 22 includes a normal observation mode filter 22a and a special observation mode filter 22b corresponding to the modes.

The normal observation mode filter 22a is provided, for example, in the inner peripheral portion of the rotary filter 22. The normal observation mode filter 22a includes a blue color filter (B) having a spectral transmittance of 380 nm to 560 nm, a green color filter (G) having a spectral transmittance of 450 nm to 630 nm, and a red color filter (R) having a spectral transmittance of 580 nm to 760 nm. Accordingly, in a case in which the normal observation mode filter 22a is disposed on the optical path of the white light, light beams of the respective colors of B, G, and R are sequentially emitted to the subject 11.

For example, the special observation mode filter 22b is provided in the outer peripheral portion of the rotary filter 22, and includes a narrowband filter that transmits blue narrowband light of 473±10 nm, a green color filter (G) having a spectral transmittance of 450 nm to 630 nm, a red color filter (R) having a spectral transmittance of 580 nm to 760 nm, and a light shielding part that blocks light in the entire wavelength band. Accordingly, in a case in which the special observation mode filter 22b is disposed on the optical path of the white light, blue narrowband light, G light, and R light are sequentially emitted to the subject 11, and then the white light is blocked.

The blue narrowband light has a wavelength band where the absorption coefficient is changed by the oxygen saturation of hemoglobin (blood hemoglobin) contained in the blood of the subject 11, and an image signal obtained by imaging the subject 11 with reflected light of the blue narrowband light is used for the calculation of the oxygen saturation of the subject 11. Accordingly, the blue narrowband light is signal light for calculating the oxygen saturation, and the broadband light source 21 and the rotary filter 22 for emitting the blue narrowband light to the subject form a signal light source.

The excitation light source 23 is a light emitting diode (LED) for emitting narrowband ultraviolet light of, for example, 340±10 nm to the subject 11. The ultraviolet light emitted from the excitation light source 23 is incident on the light guide (LG) 26 through optical members, such as a condensing lens, an optical fiber, and a multiplexer, is guided into the dark box 16, and is uniformly emitted to the subject 11 through the illumination lens 27. The excitation light source 23 is turned on in synchronization with the timing at which the white light emitted from the broadband light source 21 is blocked by the light shielding part of the special observation mode filter 22b, and emits excitation light to the subject 11.

Figure 3:
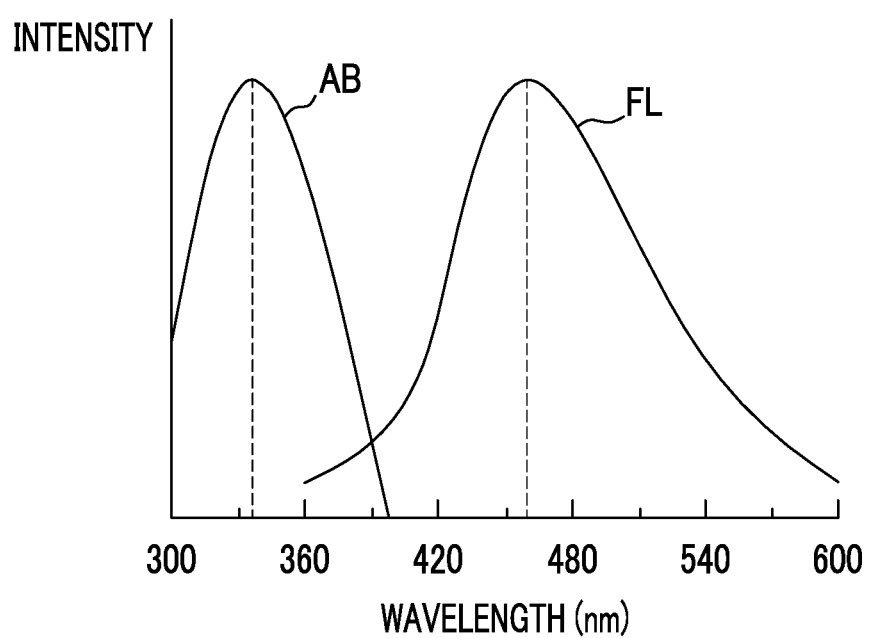
FIG. 3 is a graph showing the absorption and emission spectrums of nicotinamide adenine dinucleotide.

As shown in FIG. 3, the ultraviolet light emitted from the excitation light source 23 has a wavelength band (refer to reference numeral AB) that is absorbed by reduced nicotinamide adenine dinucleotide (NADH), and approximately blue-white fluorescence FL having a peak near 460 nm is emitted by exciting the NADH. That is, the ultraviolet light emitted from the excitation light source 23 is excitation light for making the fluorescence FL emitted from the NADH.

Nicotinamide adenine dinucleotide is an electron carrier that functions as a coenzyme of dehydrogenase, and is naturally contained in the subject 11. Although the reduced nicotinamide adenine dinucleotide (NADH) emits autofluorescence by the irradiation of excitation light emitted from the excitation light source 23 as described above, oxidized nicotinamide adenine dinucleotide ($NAD^+$) hardly absorbs the ultraviolet light emitted from the excitation light source 23. Therefore, in the fluorescence observation device 10, a tissue in which the NADH is present in high concentration, for example, cancer cells, can be observed by the fluorescence FL.

The imaging unit 13 includes an imaging lens 31, a zoom lens 32, an excitation light cut-off filter 33, and the image sensor 34, and images the subject 11 in the dark box 16.

Reflected light RL from the subject 11 or the fluorescence FL emitted from the subject 11 is incident on the image sensor 34 through the imaging lens 31, the zoom lens 32, and the excitation light cut-off filter 33. Accordingly, a reflected image of the subject 11 or a fluorescent image of the subject 11 is formed on the image sensor 34. The zoom lens 32 is provided between the tele end and the wide end, and enlarges or reduces the image of the subject 11 formed on the image sensor 34.

Figure 4:
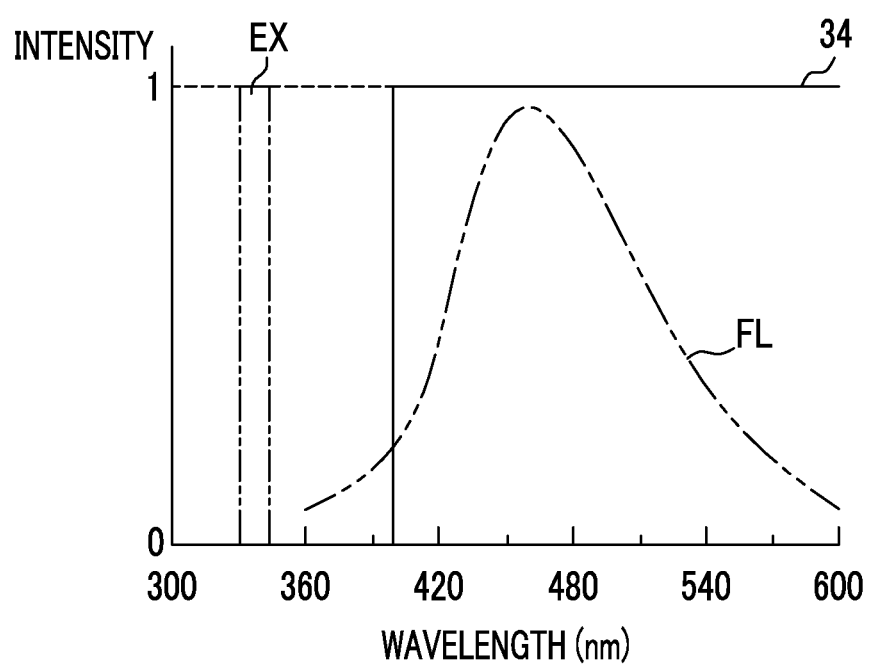
FIG. 4 is a graph showing excitation light and the spectrum of an excitation light cut-off filter.

As shown in FIG. 4, the excitation light cut-off filter 33 is an optical filter that cuts light in a wavelength band of 400 nm or less and transmits light in a wavelength band of 400 nm or more. That is, the excitation light cut-off filter 33 cuts reflected light of excitation light EX, which is emitted to the subject 11 from the excitation light source 23, and transmits the fluorescence FL emitted from the NADH. Accordingly, in the case of emitting the excitation light EX to the subject 11, an image based on the fluorescence FL emitted from the subject 11 is formed on the image sensor 34.

The excitation light cut-off filter 33 transmits blue narrowband light (473 nm) and light in the wavelength band of each of G and R emitted to the subject 11 by the broadband light source 21 and the rotary filter 22, and almost transmits light in the wavelength band of B to the extent that there is no problem in the observation of the subject 11. For this reason, even if the excitation light cut-off filter 33 is disposed, the image sensor 34 can image the subject 11 with the reflected light of each color of B, G, and R or the reflected light of blue narrowband light.

The image sensor 34 images the subject 11 by photoelectrically converting the image of the subject 11 in each of a plurality of pixels, and outputs the image signal to the processor unit 14. The image sensor 34 is, for example, a charge coupled device (CCD) image sensor or a complementary metal-oxide semiconductor (CMOS) image sensor. The image sensor 34 is a monochrome sensor in which no color filter is provided.

Figure 5:
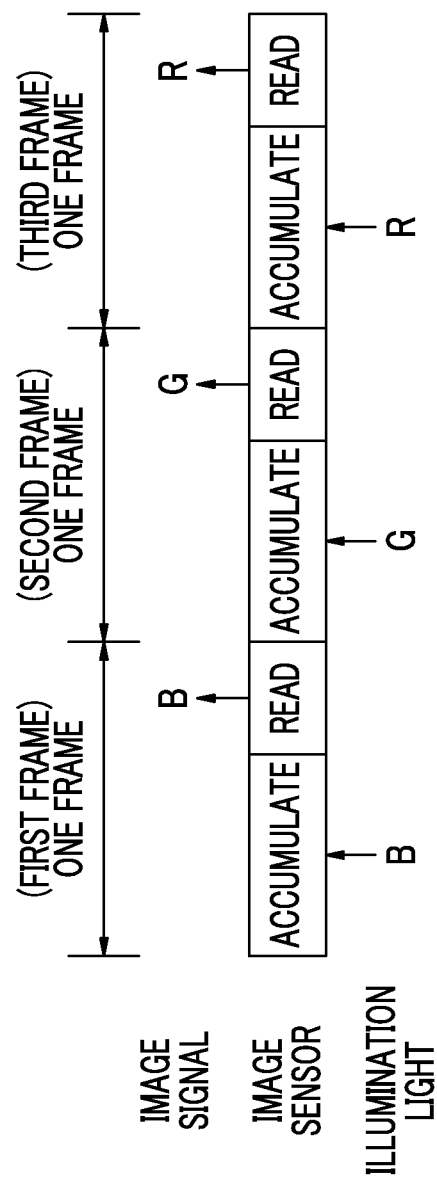
FIG. 5 is an explanatory diagram showing the imaging control in a normal observation mode.

One frame period of the image sensor 34 includes an accumulation period, for which electric charges are accumulated by photoelectrically converting the reflected light from the subject 11, and a readout period, for which accumulated electric charges are read to output an image signal. Imaging by the image sensor 34 is performed in synchronization with the rotation of the rotary filter 22. As shown in FIG. 5, in the normal observation mode, light beams of the respective colors of B, G, and R are sequentially emitted to the subject 11 for each one frame period. Therefore, the image sensor 34 images the subject 11 with the reflected light of B and outputs a B image signal in the first frame, and images the subject 11 with the reflected light of G and outputs a G image signal in the second frame. Then, the image sensor 34 images the subject 11 with the reflected light of R and outputs an R image signal in the third frame.

Figure 6:
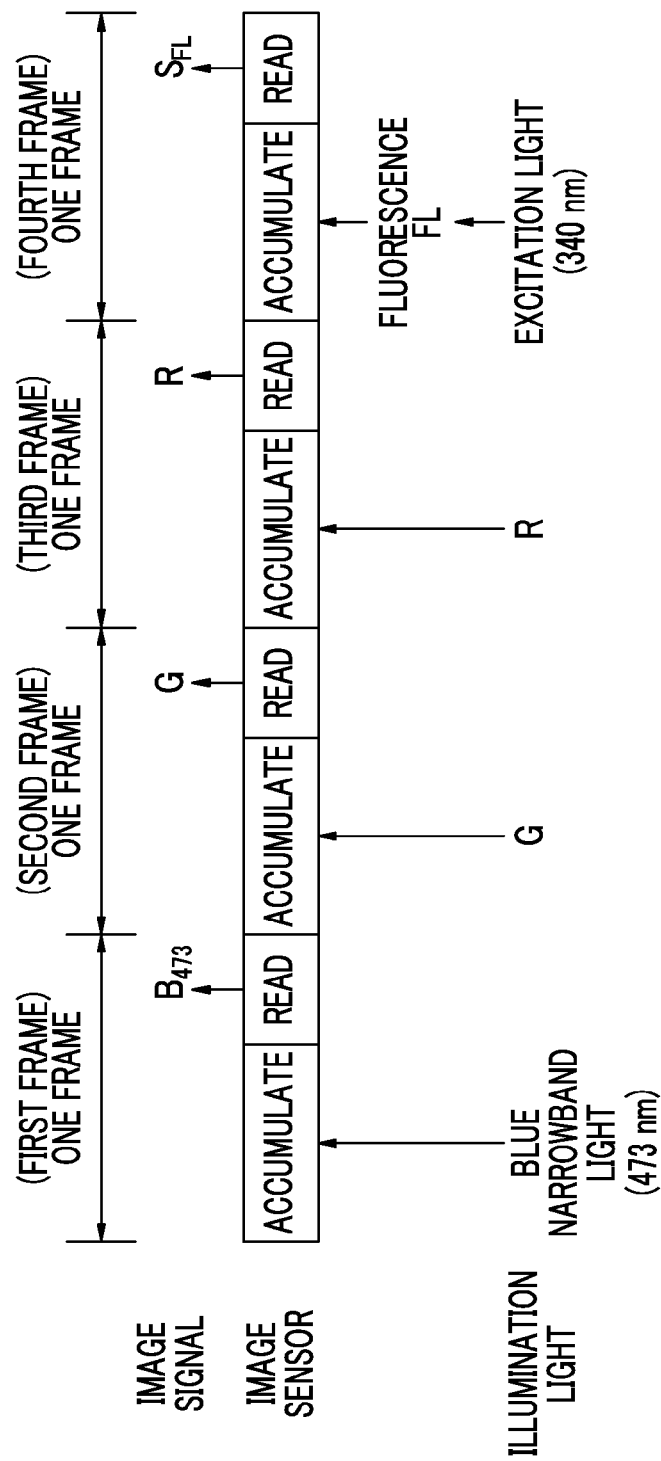
FIG. 6 is an explanatory diagram showing the imaging control in a special observation mode.

As shown in FIG. 6, in the special observation mode, blue narrowband light, G, R, and excitation light are sequentially emitted to the subject 11 for each one frame period. Accordingly, the image sensor 34 images the subject 11 with the reflected light of blue narrowband light and outputs a $B_{473}$ image signal in the first frame. In the second and third frames, the image sensor 34 images the subject 11 with the reflected light G and R and outputs a G image signal and an R image signal. In the fourth frame, light from the broadband light source 21 is blocked, and only the excitation light is emitted to the subject 11. Accordingly, reflected light of the excitation light and the fluorescence FL emitted from the subject 11 are incident on the imaging unit 13. However, since the reflected light of the excitation light is cut by the excitation light cut-off filter 33, the image sensor 34 images the subject 11 only with the fluorescence FL, and outputs a fluorescent image signal $S_{FL}$.

The processor unit 14 includes an image processing switching unit 51, a normal observation image processing unit 52, a special observation image processing unit 53, an image signal generation unit 54, a control unit 55, and an operation unit 56.

The processor unit 14 includes a receiving unit (not shown) that receives an image signal output from the image sensor 34. The receiving unit is configured to include a digital signal processor (DSP), a noise removal section, and the like. The DSP performs digital signal processing, such as color correction processing, on the received image signal. The noise removal section performs noise removal processing using, for example, a moving average method or a median filter method, on the image signal obtained by performing color correction processing or the like in the DSP. The image signal after removing the noise as described above is input to the image processing switching unit 51.

In a case in which the normal observation mode is set, the image processing switching unit 51 inputs the image signal to the normal observation image processing unit 52. On the other hand, in a case in which the special observation mode is set, the image processing switching unit 51 inputs the image signal to the special observation image processing unit 53. The setting of the observation mode is performed by the setting input using the operation unit 56, for example.

The normal observation image processing unit 52 includes a color conversion section 61, a color enhancement section 62, and a structure enhancement section 63. The color conversion section 61 generates RGB image data by assigning each image signal, which is obtained by reflected light of the light of each color of RGB input in a sequential manner, to R, G, and B pixels. Then, color conversion processing, such as 3×3 matrix processing, gradation conversion processing, and three-dimensional LUT processing, is performed on the RGB image data.

The color enhancement section 62 performs various kinds of color enhancement processing on the RGB image data after the color conversion processing. The structure enhancement section 63 performs structure enhancement processing, such as spatial frequency enhancement, on the RGB image data after the color enhancement processing. The RGB image data having been subjected to the structure enhancement processing by the structure enhancement section 63 is input to the display image signal generation unit 54 as a normal observation image.

The special observation image processing unit 53 includes a signal ratio calculation section 71, a correlation storage section 72, an oxygen saturation calculation section 73, a reference region setting section 74, a region-of-interest setting section 75, a normalized fluorescence intensity calculation section 76, a fluorescent image generation section 77, and a structure enhancement section 78.

The signal ratio calculation section 71 calculates the signal ratio of image signal used for the calculation of oxygen saturation. Specifically, the signal ratio calculation section 71 calculates the signal ratio $B_{473}/G$ between the $B_{473}$ image signal and the G image signal and the signal ratio R/G between the R image signal and the G image signal for each pixel.

Figure 7:
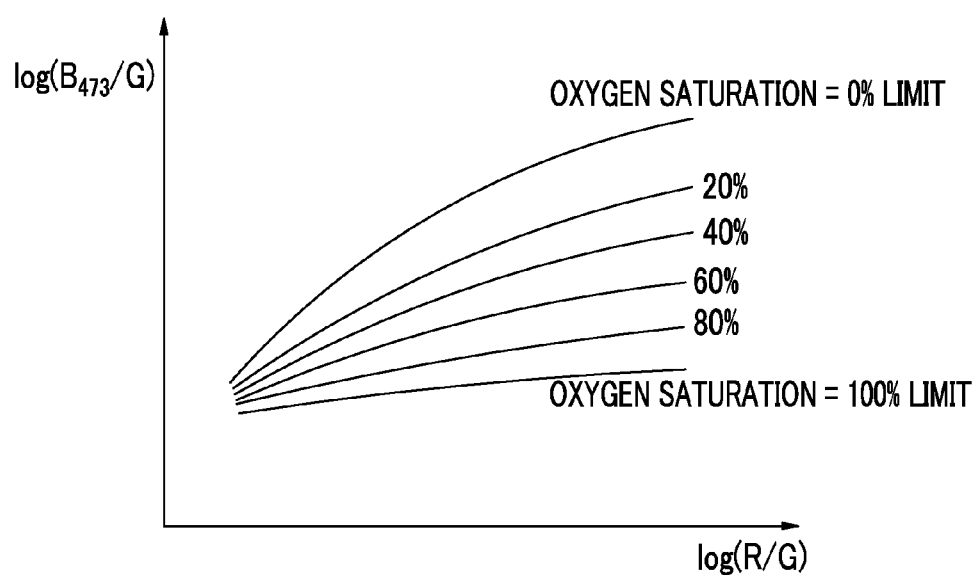
FIG. 7 is a graph showing the correlation between the signal ratio and the oxygen saturation.

The correlation storage section 72 stores the correlation between the oxygen saturation and the signal ratios $B_{473}/G$ and R/G calculated by the signal ratio calculation section 71. For example, as shown in FIG. 7, the correlation storage section 72 stores the correlation between the signal ratios $B_{473}/G$ and R/G and the oxygen saturation in the form of a two-dimensional table that defines the correlation in isolines on the two-dimensional space. The position and shape of each isoline are obtained in advance by physical simulation of light scattering. The distance between isolines changes according to the blood volume (signal ratio R/G). In the present embodiment, the correlation between the signal ratios $B_{473}/G$ and R/G and the oxygen saturation is stored in a log scale.

Figure 8:
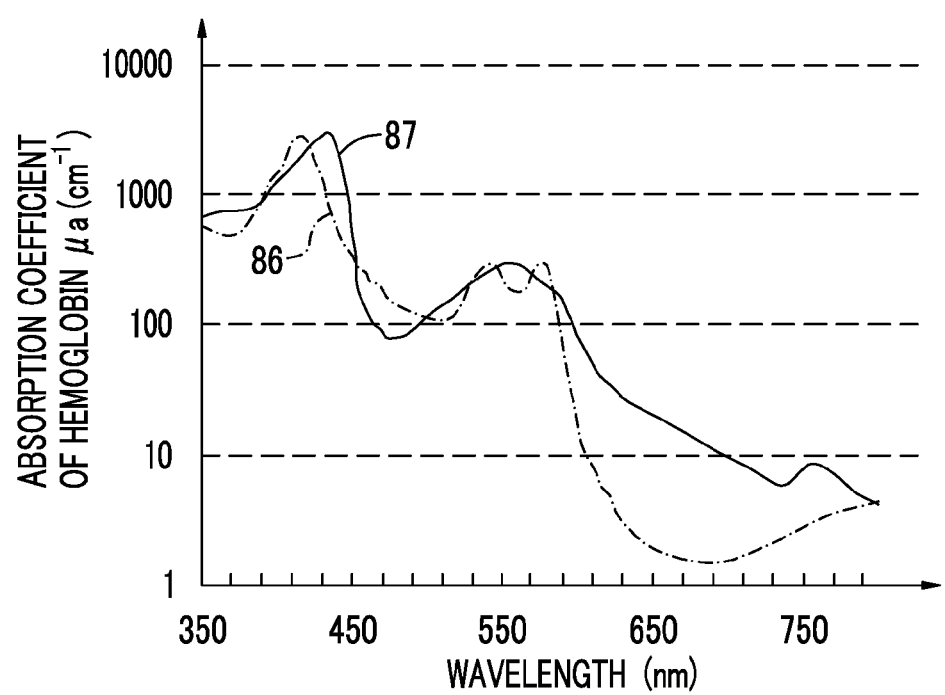
FIG. 8 is a graph showing the absorption coefficients of oxygenated hemoglobin and reduced hemoglobin.

As shown in FIG. 8, this correlation is closely related to the absorption characteristics or light scattering characteristics of oxygenated hemoglobin (graph 86) or reduced hemoglobin (graph 87). For example, as at a center wavelength of 473 nm of the blue narrowband light, at a wavelength at which the difference between the absorption coefficient of oxygenated hemoglobin and the absorption coefficient of reduced hemoglobin is large, it is easy to handle the information of oxygen saturation. However, the $B_{473}$ image signal obtained by performing imaging at the center wavelength of 473 nm of the blue narrowband light has a high dependence not only on the oxygen saturation but also on the blood volume. Therefore, by using the signal ratios $B_{473}/G$ and R/G obtained from the $B_{473}$ image signal, the R image signal corresponding to light that changes mainly depending on the blood volume, and the G image signal that is a reference signal of the $B_{473}$ image signal and the R image signal, it is possible to accurately calculate the oxygen saturation without there being dependency on the blood volume.

Figure 9:
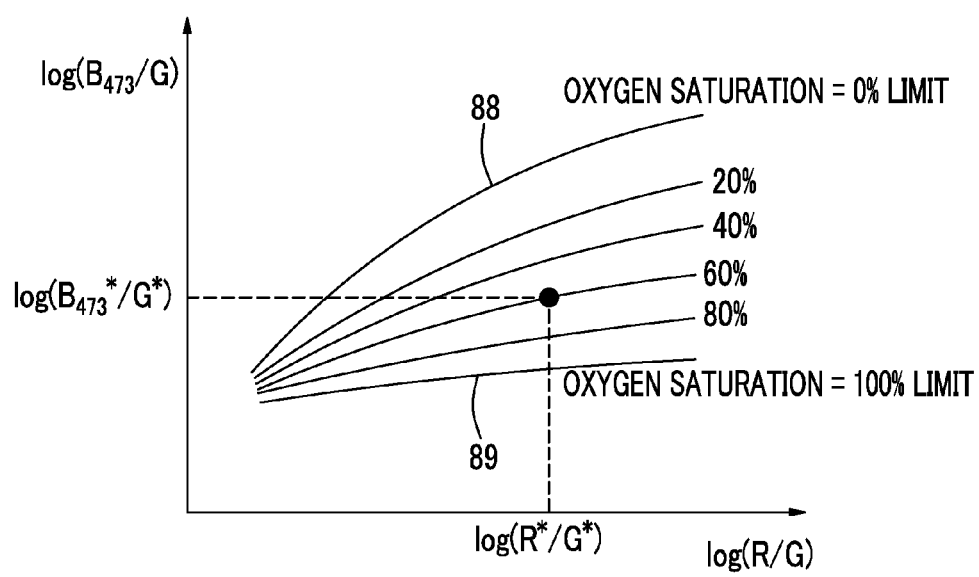
FIG. 9 is an explanatory diagram showing a method of calculating the oxygen saturation.

The oxygen saturation calculation section 73 calculates an oxygen saturation, which corresponds to the signal ratios $B_{473}/G$ and R/G calculated by the signal ratio calculation section 71, for each pixel with reference to the correlation stored in the correlation storage section 72. For example, as shown in FIG. 9, in a case in which the signal ratios in a predetermined pixel are signal ratios $B_{473}*/G*$ and $R*/G*$, the oxygen saturation corresponding to the signal ratios $B_{473}*/G*$ and $R*/G*$ is calculated to be "60%".

In addition, a case in which the signal ratios $B_{473}/G$ and R/G become extremely large or extremely small hardly occurs. That is, a case hardly occurs in which the value of the signal ratio $B_{473}/G$ or the signal ratio R/G exceeds the lower limit line 88 of the oxygen saturation of 0% or on the contrary becomes lower than the upper limit line 89 of the oxygen saturation of 100%. Here, the oxygen saturation calculation section 73 sets the oxygen saturation to 0% in a case in which the calculated oxygen saturation exceeds the lower limit line 88, and sets the oxygen saturation to 100% in a case in which the calculated oxygen saturation is lower than the upper limit line 89. In a case in which the point corresponding to the signal ratios $B_{473}/G$ and R/G deviates from a region between the lower limit line 88 and the upper limit line 89, display showing that the reliability of the oxygen saturation in the pixel is low may be performed.

The reference region setting section 74 sets a reference region of the subject 11 based on the oxygen saturation. Specifically, the reference region setting section 74 specifies a region where the oxygen saturation falls within a normal range, and sets the region as a reference region. The normal range is the range of oxygen saturation that the normal tissue which is not a lesion, such as cancer, can take. For example, the normal range is the range of 70% to 80%. That is, the reference region setting section 74 sets a region where there is a normal tissue, as a reference region, based on the oxygen saturation. There is almost no individual difference due to the subject 11 in the range of the oxygen saturation of normal tissue. Accordingly, the reference region setting section 74 can accurately specify a certain region of the normal tissue by using the oxygen saturation and set the region as a reference region. In the case of the light quantity of fluorescence FL emitted from the normal tissue, completely different values may be obtained according to individual differences if the light quantities are compared between different subjects. However, in the case of comparing the light quantities between different tissues in the same subject 11 (for example, normal tissue and cancer tissue), the light quantity of the fluorescence FL emitted from the normal tissue becomes a good standard typical of the subject 11.

The region-of-interest setting section 75 sets a region of interest of the subject 11 based on the oxygen saturation. Specifically, the region-of-interest setting section 75 specifies a region where the oxygen saturation is an abnormal value deviating from the normal range by a predetermined value or more, and sets the region as a region of interest. The normal range of the oxygen saturation is a range of about 70% to 80% without individual difference due to the subject 11 described above. Accordingly, the region-of-interest setting section 75 sets, for example, a region where the oxygen saturation is lower than that in other regions by 10% or more (region where the oxygen saturation is 60% or less) as a region of interest. For example, since cancer tissue is in a low oxygen state, the cancer tissue is set as a region of interest by the region-of-interest setting section 75.

The normalized fluorescence intensity calculation section 76 normalizes the emission intensity of the fluorescence FL by diseased tissue having an abnormal oxygen saturation based on the emission intensity of the fluorescence FL by normal tissue. Specifically, the normalized fluorescence intensity calculation section 76 extracts the pixel value (that is, the emission intensity of the fluorescence FL) of each pixel in the set reference region from the fluorescent image signal $S_{FL}$, calculates the average value, and sets the value as the reference fluorescence intensity of the fluorescence FL by the subject 11. The reference fluorescence intensity of the fluorescence FL corresponds to the normal content of NADH, and is a unique value that characterizes the subject 11. In addition, the normalized fluorescence intensity calculation section 76 extracts the pixel value of each pixel in the set region of interest from the fluorescent image signal $S_{FL}$, calculates the average value, and sets the value as the emission intensity of the fluorescence FL in the region of interest (hereinafter, referred to as a region-of-interest fluorescence intensity). Then, the normalized fluorescence intensity calculation section 76 normalizes the region-of-interest fluorescence intensity by dividing the region-of-interest fluorescence intensity by the reference fluorescence intensity. This value is referred to as the normalized fluorescence intensity hereinafter.

The fluorescent image generation section 77 generates a fluorescent image showing the emission intensity of the fluorescence FL visually using the $B_{473}$ image signal, the G and R image signals, and the normalized fluorescence intensity calculated by the normalized fluorescence intensity calculation section 76. Specifically, the fluorescent image generation section 77 applies a gain corresponding to the normalized fluorescence intensity to the pixel value of each pixel in the region of interest of the $B_{473}$ image signal, and generates RGB image data using the G and R image signals and the $B_{473}$ image signal to which the gain has been applied. The RGB image data generated using the G and R image signals and the $B_{473}$ image signal to which the gain has been applied is a fluorescent image. For example, the fluorescent image generation section 77 multiplies the pixel value of each pixel in the region of interest of the $B_{473}$ image signal by the value of the normalized fluorescence intensity (or a value obtained by multiplying the normalized fluorescence intensity by an appropriate number) as a gain. Accordingly, in the RGB image data generated by the fluorescent image generation section 77, the region of interest is displayed in a pseudo-color that is colored in blue with the density corresponding to the normalized fluorescence intensity, and a region other than the region of interest is displayed in a normal color (color in a case in which the region is observed under white light).

In addition, the fluorescent image generation section 77 generates a fluorescent image, in which the entire region of interest is uniformly colored, using the normalized fluorescence intensity. However, such pseudo-coloring may be performed for each pixel. For example, the normalized fluorescence intensity calculation section 76 generates a normalized fluorescent image signal $N_{FL}$ by performing normalization by dividing each pixel value of the fluorescent image signal $S_{FL}$ by the calculated reference fluorescence. The normalized fluorescent image signals $N_{FL}$, is a collection of the normalized fluorescence intensities of the respective pixels. Then, the fluorescent image generation section 77 multiplies each pixel of the $B_{473}$ image signal by each pixel value of the normalized fluorescent image signal $N_{FL}$ as a gain, and generates a fluorescent image using the G and R image signals and the $B_{473}$ image signal that has been multiplied by the normalized fluorescent image signal $N_{FL}$. Since each pixel of the fluorescent image is pseudo-colored based on the normalized emission intensity in this manner, it is possible to observe the emission distribution of the fluorescence FL in more detail. Needless to say, also in the case of using the normalized fluorescent image signal $N_{FL}$ as described above, only the region of interest may be pseudo-colored. This is because there is a case in which only the emission intensity of the fluorescence FL in the region of interest is information contributing to diagnosis and the emission intensity of the fluorescence FL in a region other than the region of interest is noise at the time of diagnosis. However, if a fluorescent image, in which the entire region of interest is uniformly colored using the normalized fluorescence intensity, is generated, it is easy to identify the region of interest. Therefore, in order to present a region of interest so as to be easily understood, it is preferable to generate a fluorescent image in which the entire region of interest is uniformly colored using the normalized fluorescence intensity.

The structure enhancement section 78 performs structure enhancement processing, such as spatial frequency enhancement processing, on the fluorescent image input from the fluorescent image generation section 77. The fluorescent image having been subjected to the structure enhancement processing by the structure enhancement section 78 is input to the display image signal generation unit 54.

The display image signal generation unit 54 converts the normal observation image or the fluorescent image into a display format signal (display image signal), and inputs the display format signal to the monitor 15. As a result, the normal observation image or the fluorescent image is displayed on the monitor 15.

The control unit 55 performs overall control of each unit of the fluorescence observation device 10. For example, the control unit 55 controls the position (switching between the normal observation mode filter 22a and the special observation mode filter 22b) or the rotation speed of the rotary filter 22, the imaging of the image sensor 34, the image processing switching of the image processing switching unit 51, and the zoom lens 32 based on the input from the operation unit 56. The operation unit 56 is a user interface (UI) for receiving an input operation, such as a function setting. A recording unit (not shown) in which an image, information attached to the image, and the like are recorded may be connected to the processor unit 14.

Figure 10:
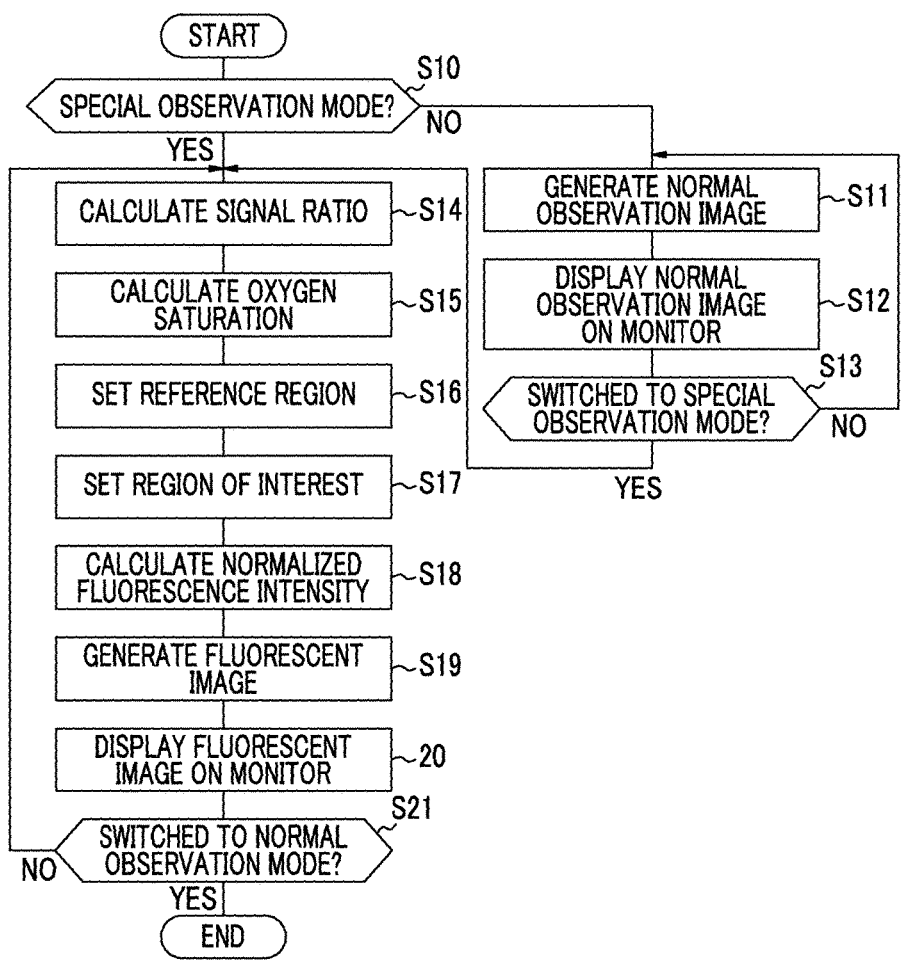
FIG. 10 is a flowchart showing the operation of the fluorescence observation device.

Next, the flow of observation using the fluorescence observation device 10 of the present embodiment will be described with reference to the flowchart in FIG. 10. First, in a case in which the normal observation mode is set (S10; NO), light beams of the respective colors of B, G, and R are sequentially emitted to the subject 11, and the image sensor 34 images the subject 11 with reflected light beams thereof and outputs B, G, and R image signals. Then, a normal observation image is generated from the B, G, and R image signals (S11), and is displayed on the monitor 15 (S12). The generation and display of the normal observation image are repeatedly performed until the observation mode is switched to the special observation mode (S13).

Figure 11:
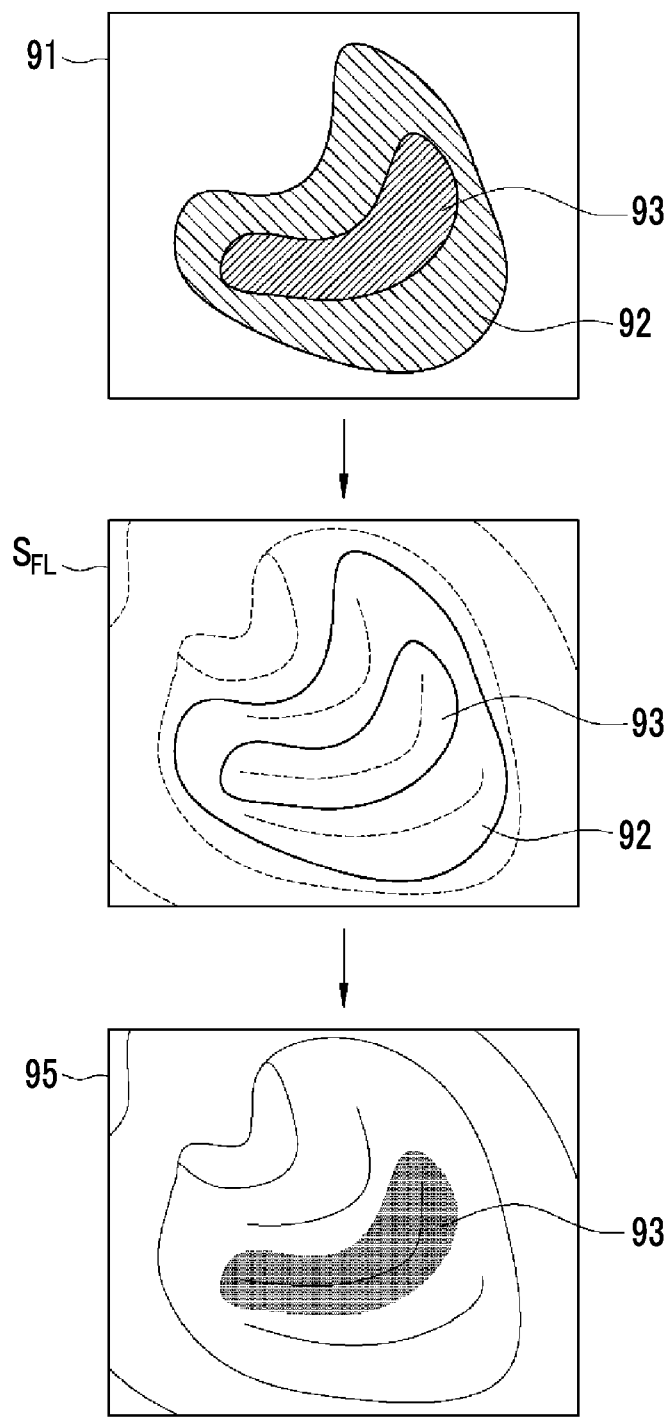
FIG. 11 is an explanatory diagram showing a reference region, a region of interest, and a fluorescent image.

On the other hand, in a case in which the observation mode is set to the special observation mode (S10; YES), blue narrowband light, G light, R light, and the excitation light EX are sequentially emitted to the subject 11, and the image sensor 34 images the subject 11 with reflected light beams thereof or the fluorescence FL emitted from the subject 11 and outputs the $B_{473}$ image signal, the G image signal, the R image signal, and the fluorescent image signal S. When these image signals are obtained from the image sensor 34, the signal ratio calculation section 71 calculates the signal ratios $B_{473}/G$ and R/G (S14), and the oxygen saturation calculation section 73 calculates the oxygen saturation 91 of the subject 11 for each pixel based on the signal ratios $B_{473}/G$ and R/G as shown in FIG. 11 (S15). When the oxygen saturation 91 is calculated, the reference region setting section 74 sets a reference region 92 (refer to FIG. 11) of the subject 11 by specifying a region where the value of the oxygen saturation falls within a specific range (S16). The region-of-interest setting section 75 sets a region of interest 93 (refer to FIG. 11) of the subject 11 by specifying a region, in which the value of the oxygen saturation is an abnormal value deviating from the above specific range by a predetermined value or more, using the oxygen saturation 91 (S17).

When the reference region 92 and the region of interest 93 of the subject 11 are set as described above, the normalized fluorescence intensity calculation section 76 calculates a reference fluorescence intensity by extracting the pixel value of the reference region 92 from the fluorescent image signal $S_{FL}$ and calculating the average value. In addition, the normalized fluorescence intensity calculation section 76 calculates a region-of-interest fluorescence intensity by extracting the pixel value in the region of interest 93 and calculating the average value. Then, a normalized fluorescence intensity is calculated by performing normalization by dividing the region-of-interest fluorescence intensity by the reference fluorescence intensity (S18).

Then, the fluorescent image generation section 77 multiplies each pixel value in the region of interest 93 of the $B_{473}$ image signal by the normalized fluorescence intensity as a gain, and generates a fluorescent image 95 (refer to FIG. 11) using the $B_{473}$ image signal multiplied by the normalized fluorescence intensity and the G and R image signals (S19). The fluorescent image 95 is an image in which the region of interest 93 is pseudo-colored according to the normalized fluorescence intensity, and shows the region of interest 93 and shows the emission intensity of the region of interest 93 with the color.

The generated fluorescent image 95 is sequentially displayed on the monitor 15 (S20). Such generation and display of the fluorescent image 95 are repeatedly performed until the observation mode is switched to the normal observation mode or until the observation of the subject 11 ends (S21).

As described above, the fluorescence observation device 10 sets the reference region 92 and the region of interest 93 based on the oxygen saturation 91 of the subject 11, and calculates a reference fluorescence intensity unique to the subject 11 from the emission intensity of the fluorescence FL in the reference region 92. Then, based on the normalized fluorescence intensity calculated by normalizing the region-of-interest fluorescence intensity indicating the emission intensity of the region of interest 93 using the reference fluorescence intensity, the fluorescent image 95 in which the region of interest 93 is pseudo-colored is generated and displayed. Therefore, the fluorescence observation device 10 can display the emission intensity (content of NADH) of the fluorescence FL unique to the subject 11 in pseudo-color, rather than the comparison with other subjects.

For example, an individual in which the content of NADH is originally large cannot be immediately determined that there is a lesion, such as cancer tissue, even if the emission intensity of the fluorescence FL is simply high. In contrast, an individual in which the content of NADH is originally low may include a lesion, such as cancer tissue, even if the emission intensity of the fluorescence FL is low. For this reason, even if the emission intensity of the fluorescence FL of the subject 11 under observation is compared with those of other subjects, for example, standard data as in the conventional fluorescence observation device, it is not possible to accurately specify abnormalities unique to the subject 11 under observation. However, according to the fluorescence observation device 10, it is possible to accurately display a lesion regardless of individual differences of the subject 11.

In addition, since the emission intensity of fluorescence FL is greatly influenced by individual differences of the subject 11, it is difficult to set the reference region 92 or the region of interest 93 from the emission intensity of the fluorescence FL. For example, if a region where the emission intensity of the fluorescence FL is higher than a predetermined threshold value is set to the region of interest, a larger region than the actual diseased tissue is set as a region of interest in a case in which the subject 11 is an individual in which the content of NADH is originally large. On the other hand, since the fluorescence observation device 10 sets the reference region 92 or the region of interest 93 based on the oxygen saturation that hardly depends on the individual differences of the subject 11, it is possible to accurately set the reference region 92 or the region of interest 93. Therefore, the fluorescence observation device 10 can show a region of a correct lesion, as the region of interest 93, in the fluorescent image 95 without excess or deficiency.

In the fluorescence observation device 10, the subject 11 is observed by the fluorescence FL of NADH. However, the subject 11 may also be observed by fluorescence emitted from other fluorescent materials. For example, it is possible to observe the subject 11 with fluorescence based on autofluorescent materials, such as flavin adenine dinucleotide (FAD), thyrosin, tryptophan, phenylalanine, collagen, porphyrin, elastin, melanin, lipofuscin, ceroid, pyridoxine, and eosinophils. A fluorescent material may be administered, injected, or sprayed (hereinafter, referred to as administered) to the subject 11, so that the subject 11 is observed by its fluorescence. In addition, a non-fluorescent material having a content or activity that changes in correlation with the use of oxygen in the metabolic system may be replaced with a fluorescent material by genetic manipulation, so that the subject 11 is observed by its fluorescence. Thus, in the case of observing the subject 11 with the fluorescence based on each fluorescent material other than NADH, the excitation light source 23 or the excitation light cut-off filter 33 may be replaced according to the type of the fluorescent material. The subject 11 may also be able to be observed by fluorescence based on a plurality of types of fluorescent materials. In this case, a corresponding excitation light source or a corresponding excitation light cut-off filter may be provided.

The normalized fluorescence intensity calculation section 76 averages the pixel values of the reference region and the region of interest of the fluorescent image signal $S_{FL}$, and sets the value as the reference fluorescence intensity and the region-of-interest fluorescence intensity that are used for normalization. However, instead of the average value, a maximum value, a minimum, a median, or the like may be used as the reference fluorescence intensity and the region-of-interest fluorescence intensity. The reference fluorescence intensity and the region-of-interest fluorescence intensity may be calculated in different methods. For example, the reference fluorescence intensity may be calculated using an average, and the maximum value may be adopted for the region-of-interest fluorescence intensity.

Instead of the broadband light source 21, for example, a laser light source, such as a laser diode, may also be used. In the case of using the laser light source, it is possible to emit the white light as in the broadband light source 21, for example, by using a phosphor that emits fluorescence by absorbing a part of laser light emitted from the laser light source. In addition, for example, LEDs of R, G, and B or a laser diode may be used instead of the broadband light source 21. In this case, LEDs of the respective colors or the like may be sequentially turned on and off without using the rotary filter 22.

In addition, an LED is used as the excitation light source 23. However, a mercury lamp, a metal halide lamp, an ultraviolet laser diode, or the like may be used instead of the LED.

Instead of the rotary filter 22, an interference filter, an etalon, a liquid crystal tunable filter, or the like may be used.

As the image sensor 34, a photodetector, such as a phototube or a photomultiplier tube, may be used instead of a monochrome CCD or monochrome CMOS. In addition, a color image sensor in which color filters are provided may be used. In the case of using a color image sensor as the image sensor 34, the rotary filter 22 may not be used for the light source unit 12. In the case of using a color image sensor, a primary-color image sensor in which color filters of R, G, and B are provided can be used. In addition, a complementary color image sensor including complementary color filters of cyan (C), magenta (M), yellow (Y), and green (G) may be used. In the case of using the complementary color image sensor, if a color conversion unit that performs color conversion into image signals of three colors of RGB from image signals of four colors of CMYG is provided, it is possible to obtain the image signals of three colors of RGB from the image signals of four colors of CMYG by color conversion.

In addition, the excitation light is emitted by turning on the excitation light source 23 at the timing at which the white light emitted from the broadband light source 21 is blocked. However, since the fluorescence FL is weak compared with the light quantity of reflected light of each color of RGB, the excitation light source 23 may be turned on at all times to continue the emission of excitation light.

Second Embodiment

Figure 12:
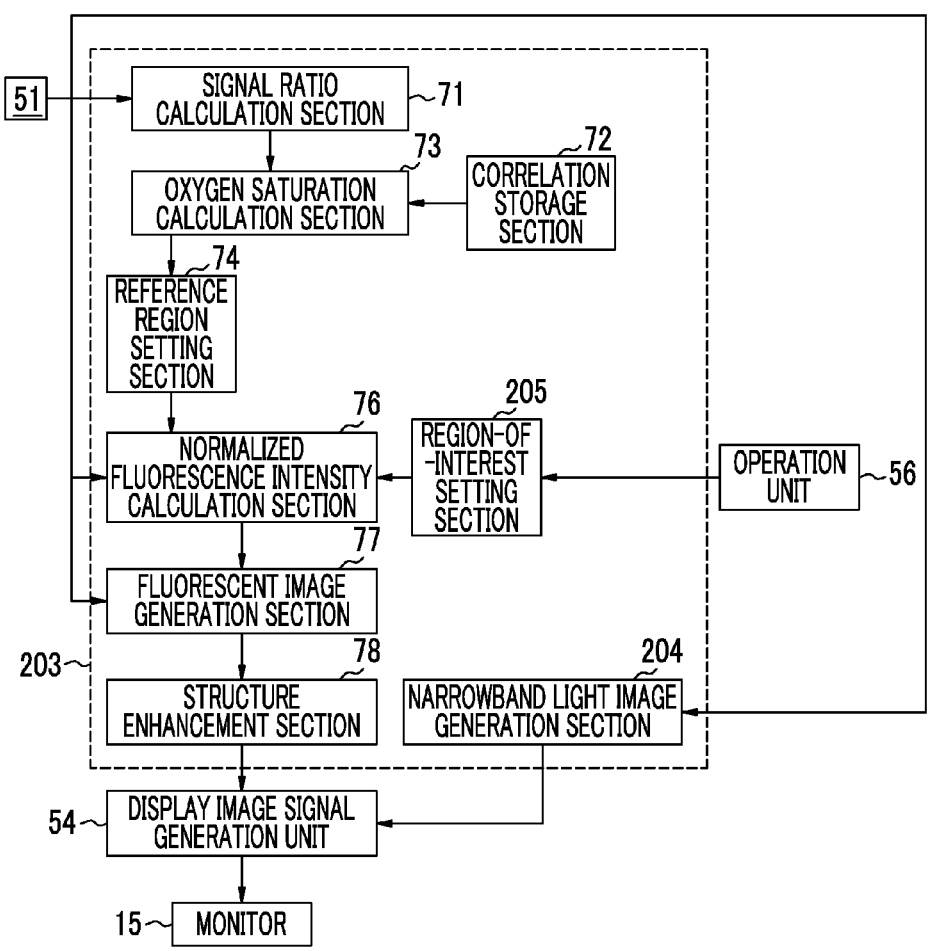
FIG. 12 is a block diagram of a special observation image processing unit of a second embodiment.

Although the fluorescence observation device 10 of the first embodiment sets the region of interest based on the oxygen saturation, the region of interest may also be set using another method that does not depend on the oxygen saturation. In this case, the special observation image processing unit 53 of the fluorescence observation device 10 is replaced with, for example, a special observation image processing unit 203 shown in FIG. 12. The other configuration is the same as that of the fluorescence observation device 10 of the first embodiment.

The special observation image processing unit 203 includes a narrowband light image generation section 204 and a region-of-interest setting section 205. A signal ratio calculation section 71, a correlation storage section 72, an oxygen saturation calculation section 73, a reference region setting section 74, a normalized fluorescence intensity calculation section 76, a fluorescent image generation section 77, and a structure enhancement section 78 other than these are the same as those in the special observation image processing unit 53 of the fluorescence observation device 10 of the first embodiment.

The narrowband light image generation section 204 acquires a $B_{473}$ image signal and a G image signal through the image processing switching unit 51, and generates a narrowband light image, for example, by assigning the $B_{473}$ image signal to B and G pixels and assigning the G image signal to the R pixel. In the narrowband light image, shape information of the subject 11, such as superficial blood vessels or ductal structures, is emphasized according to the wavelength of blue narrowband light. The generated narrowband light image is input to the display image signal generation unit 54, and is displayed on the monitor 15.

The user observes the narrowband light image displayed on the monitor 15, and designates (inputs) a region of interest based on the shape information of the subject 11. The designation of the region of interest by the user is performed by using the operation unit 56. For example, the user inputs region-of-interest designation information, such as a frame surrounding a place where the superficial blood vessels emphasized in the narrowband light image are dense, using the operation unit 56. The region-of-interest setting section 205 sets the region of interest of the subject 11 based on the region-of-interest designation information input from the operation unit 56.

By generating and displaying the narrowband light image as described above and setting the region of interest by manual designation of the user based on the shape information of the subject 11, the desired region of interest of the user in a fluorescent image can be accurately displayed in pseudo-color.

Although the narrowband light image is generated and displayed, an oxygen saturation image showing the oxygen saturation of the subject 11 may be generated and displayed instead of the narrowband light image, so that the user designates a region of interest based on the oxygen saturation image. In this case, it is preferable to provide an oxygen saturation image generation section (not shown) instead of the narrowband light image generation section 204. The oxygen saturation image generation section acquires the oxygen saturation calculated by the oxygen saturation calculation section 73, the $B_{473}$ image signal, and the G and R image signals, and applies a gain corresponding to the oxygen saturation to the $B_{473}$ image signal and the G and R image signals. Then, an oxygen saturation image is generated by assigning the $B_{473}$ image signal and the G and R image signals, to which the gain corresponding to the oxygen saturation has been applied, to the respective pixels of B, G, and R. For example, for a pixel where the oxygen saturation is less than 60%, the $B_{473}$ image signal is multiplied by the gain less than "1", and the G and R image signals are multiplied by the gain of "1" or more. For a pixel where the oxygen saturation is higher than 60%, the $B_{473}$ image signal and the G and R image signals are multiplied by the gain of "1". In this manner, an oxygen saturation image is obtained in which a region where the oxygen saturation is equal to or less than "60%" is emphasized by being pseudo-colored. Accordingly, by generating and displaying the oxygen saturation image, it is possible to make the user designate a region of interest using a region pseudo-colored in the oxygen saturation image as a guide.

In addition, a color image, which is the same as the normal observation image, may be generated and displayed using the $B_{473}$ image signal and the G and R image signals, and a region of interest may be designate based on the color image. An estimated spectral image, which is generated by estimating arbitrary wavelength band components using the $B_{473}$ image signal and the G and R image signals, may be generated and displayed, and a region of interest may be designate based on the estimated spectral image.

Figure 13:
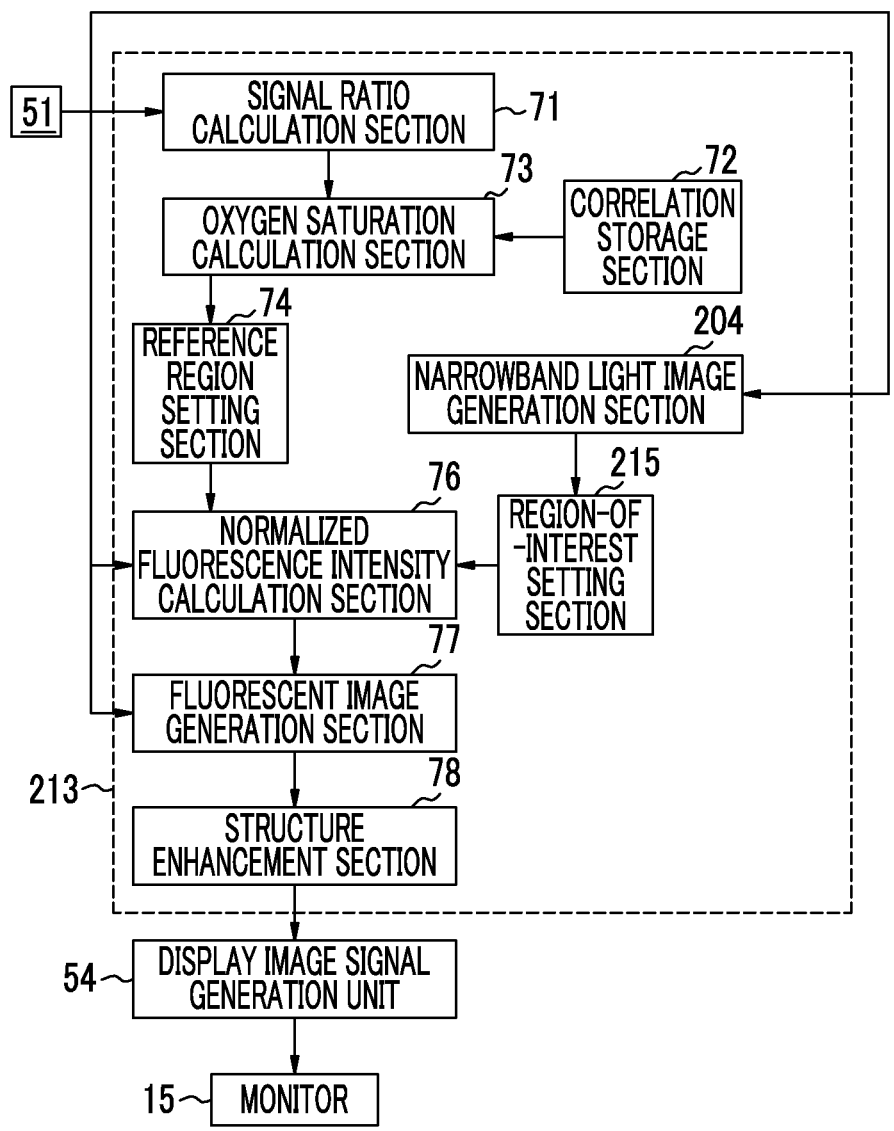
FIG. 13 is a block diagram showing a special observation image processing unit in a modification example.
Figure 14:
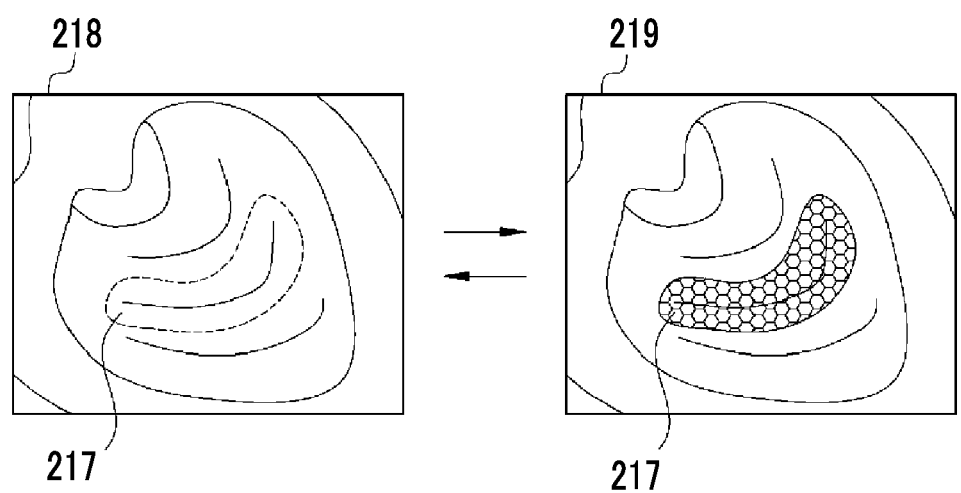
FIG. 14 is an explanatory diagram showing the operation in the modification example.

In the case of setting the region of interest using another method that does not depend on the oxygen saturation, the special observation image processing unit 53 of the fluorescence observation device 10 may be replaced with a special observation image processing unit 213 shown in FIG. 13. In the special observation image processing unit 213, a narrowband light image generated by the narrowband light image generation section 204 is input to a region-of-interest setting section 215. Then, the region-of-interest setting section 215 extracts the shape of the highlighted subject 11 from the input narrowband light image, and automatically sets the extracted part as a region of interest. For example, as shown in FIG. 14, a fine shape 217, such as superficial blood vessels or ductal structures, can be checked in a narrowband light image 219 even if the fine shape 217 is difficult to appear in the normal observation image. Accordingly, the region-of-interest setting section 215 extracts a region of the highlighted fine shape 217, and sets the region as a region of interest. The other configuration is the same as the special observation image processing unit 203 (refer to FIG. 12). Thus, according to the special observation image processing unit 213, a region of interest can be automatically set based on the shape information of the subject 11 appearing in the narrowband light image regardless of the oxygen saturation.

Instead of the narrowband light image, an oxygen saturation image or an estimated spectral image may be used. In a case in which the desired shape information can be checked in a color image that is the same as the normal observation image, a region of interest may be automatically set from the color image that is the same as the normal observation image.

Even in a case in which the region of interest is automatically set based on the narrowband light image 219, the narrowband light image 219 may be displayed on the monitor 15. If the narrowband light image 219 is displayed on the monitor 15, the user can check the region of interest that is automatically set. In a case in which the region of interest automatically set by the region-of-interest setting section 215 does not match the desired region of interest of the user, the user may designate a region of interest as in the region-of-interest setting section 205 (refer to FIG. 12) of the special observation image processing unit 203.

Figure 15:
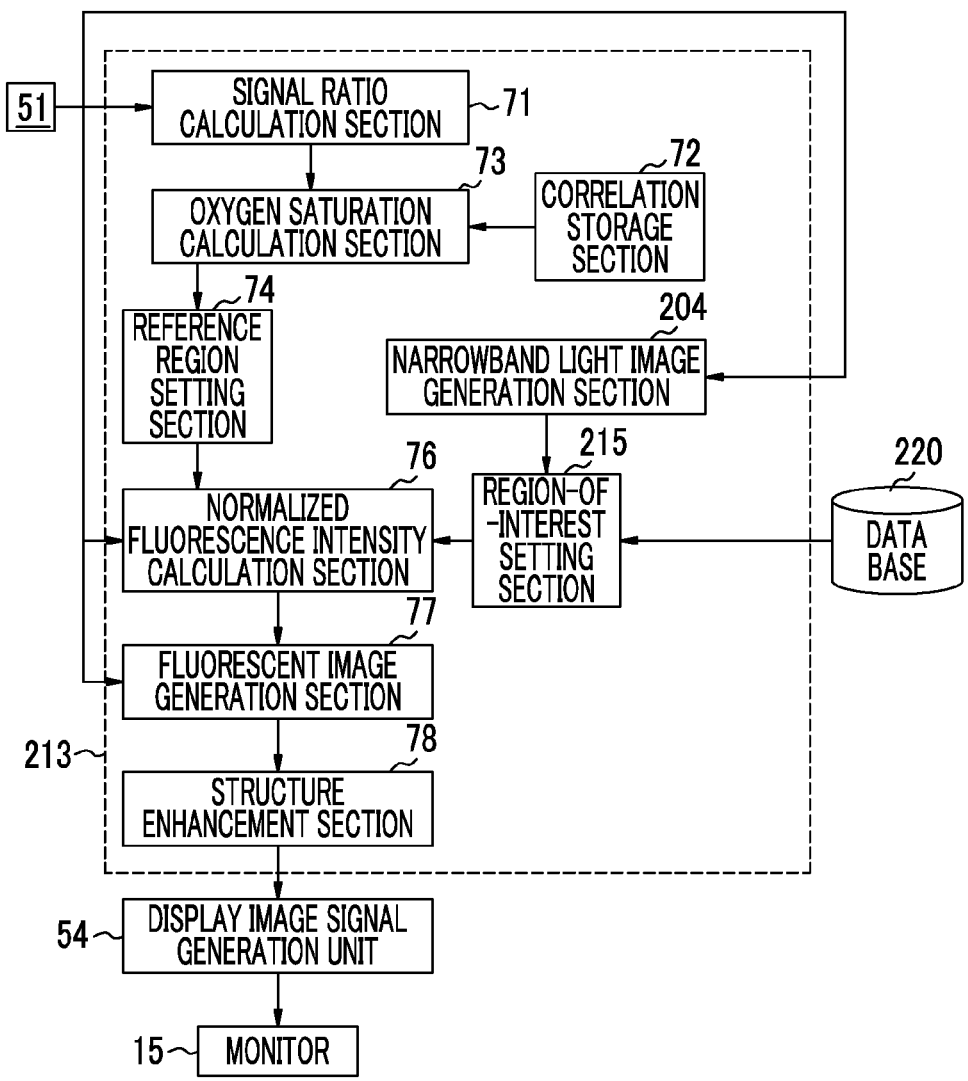
FIG. 15 is a block diagram showing a special observation image processing unit in another modification example.

In the special observation image processing unit 213, the region-of-interest setting section 215 sets the region of interest automatically based on only the narrowband light image 219. However, a region of interest may be extracted from the narrowband light image 219 based on the past cases or the like. For example, as shown in FIG. 15, the region-of-interest setting section 215 is connected to a database 220 in which the past case images (narrowband images or the like) are stored. Then, the region-of-interest setting section 215 matches the shape information of the subject 11 between the narrowband light image 219 and the past case images, extracts a region matching the characteristic shape information of the past cases from the narrowband light image 219, and sets the region as a region of interest. If a region of interest is set by comparison with the past cases as described above, a possibility is reduced that a region less relevant to the lesion will be designated as a region of interest even if the region is highlighted in the narrowband light image 219. Therefore, it is possible to improve the accuracy of the region of interest designated automatically.

The database 220 may be provided in the fluorescence observation device, or may be provided outside the fluorescence observation device, or may be connected through a communication network. Also in the case of making the user designate a region of interest (refer to FIG. 12), it is possible to assist the user in designating the region of interest by displaying the past case images on the monitor 15 using the database 220.

Third Embodiment

Figure 16:
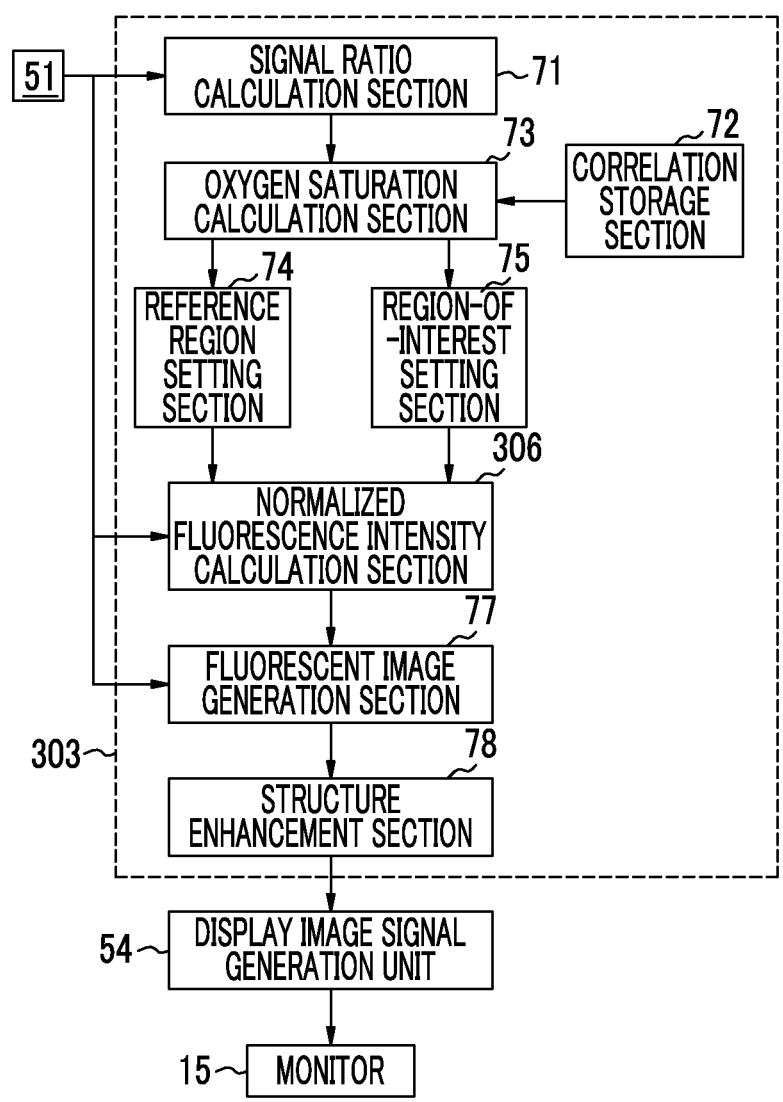
FIG. 16 is a block diagram of a special observation image processing unit of a third embodiment.

In the fluorescence observation device 10 of the first embodiment, the subject 11 is observed in real time. However, information indicating a temporal change (temporal information) may be further presented to the user. In this case, the special observation image processing unit 53 of the fluorescence observation device 10 of the first embodiment is replaced with, for example, a special observation image processing unit 303 shown in FIG. 16. In the special observation image processing unit 303, the normalized fluorescence intensity calculation section 76 of the special observation image processing unit 53 is replaced with a normalized fluorescence intensity calculation section 306, and the other configuration is the same as that of the special observation image processing unit 53. Hereinafter, it is assumed that the subject 11 is imaged at the imaging time T1, T2, T3, . . . at predetermined time intervals ΔT from the initial imaging time T1 set in advance.

The normalized fluorescence intensity calculation section 306 calculates a normalized fluorescence intensity by normalizing the fluorescence intensity of the region of interest with the fluorescence intensity of the reference region. However, the method of calculating the normalized fluorescence intensity is different from the normalized fluorescence intensity calculation section 76 of the first embodiment, and calculates the normalized fluorescence intensity that is also temporally normalized. Specifically, the normalized fluorescence intensity calculation section 306 calculates the reference fluorescence intensity based on the set reference region whenever the subject 11 is imaged. This is the same as the normalized fluorescence intensity calculation section 76 of the first embodiment. That is, the normalized fluorescence intensity calculation section 306 extracts the pixel value of a pixel in the reference region set at each imaging time from the fluorescent image signal $S_{FL}$ acquired at each imaging time, and calculates the reference fluorescence intensity at each imaging time by averaging the pixel values.

On the other hand, although the normalized fluorescence intensity calculation section 306 calculates the region-of-interest fluorescence intensity, the calculation method is different from the normalized fluorescence intensity calculation section 76. Specifically, although the normalized fluorescence intensity calculation section 76 calculates the region-of-interest fluorescence intensity by extracting the pixel value of the region of interest set at each imaging time, the normalized fluorescence intensity calculation section 306 calculates the region-of-interest fluorescence intensity at each imaging time using the region of interest set at the initial imaging time T1 (hereinafter, referred to as an initial region of interest). That is, the normalized fluorescence intensity calculation section 306 fixes a region for extracting a pixel value in order to calculate the region-of-interest fluorescence intensity to the initial region of interest instead of a region of interest at each imaging time. For example, in the case of calculating the region-of-interest fluorescence intensity at the imaging time T2, pixel values in a region corresponding to the initial region of interest are extracted from the fluorescent image signal $S_{FL}$ at the imaging time T2, and the average value is calculated to calculate the region-of-interest fluorescence intensity. This is the same for the imaging time T3 and subsequent ones.

The normalized fluorescence intensity calculation section 306 calculates a normalized fluorescence intensity by dividing the region-of-interest fluorescence intensity calculated as described above by the reference fluorescence intensity. Since the normalized fluorescence intensity is calculated by dividing the fluorescence intensity of the region of interest by the fluorescence intensity of the reference region, normalization with no individual difference of the subject 11 is made. In addition, since the region of interest is fixed to the initial region of interest, a change in the fluorescence intensity that is temporally normalized with the initial imaging time T1 as a reference is shown.

The fluorescent image generation section 77 generates a fluorescent image by pseudo-coloring the region of interest based on the normalized fluorescence intensity calculated by the normalized fluorescence intensity calculation section 306 instead of the normalized fluorescence intensity of the first embodiment. The pseudo-colored region is a region of interest set at each imaging time.

Figure 17:
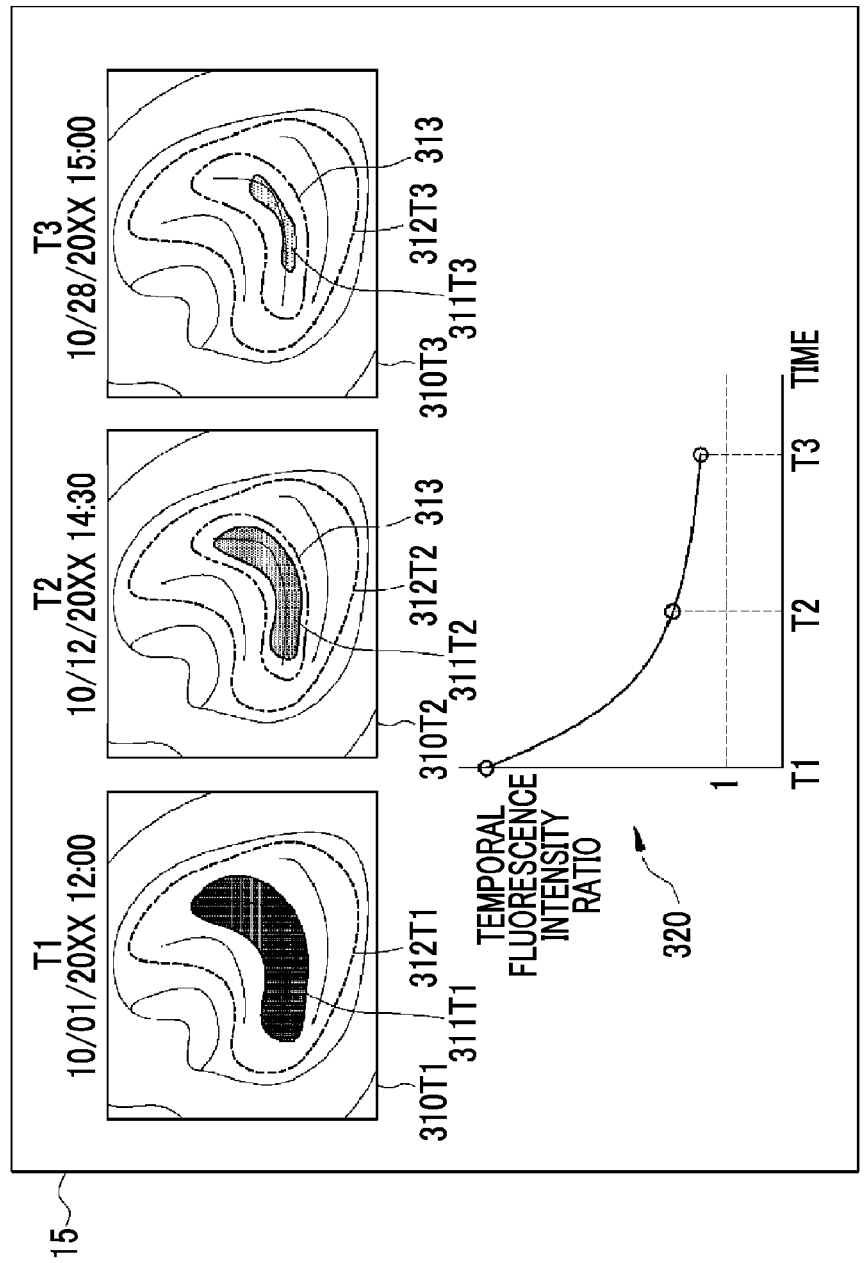
FIG. 17 is an explanatory diagram showing the monitor display of the third embodiment.

Then, as shown in FIG. 17, at least two or more of fluorescent images 310T1, 310T2, 310T3, . . . at the respective imaging times are displayed in time series on the monitor 15. By observing the fluorescent images 310T1, 310T2, 310T3, . . . at the respective imaging times, it is possible to see the change in the size of a lesion, such as cancer, through the temporal changes in the sizes of pseudo-colored regions of interest 311T1, 311T2, 311T3, . . . . In addition, the change in the color (or gradation) of the region of interest indicates a temporal change in the content of NADH. For example, if the subject 11 is observed after administering treatment drugs, such as anti-cancer drugs, to the subject 11, it is possible to determine the effect.

In these fluorescent images 310T1, 310T2, 310T3, . . . , it is preferable to display reference regions 312T1, 312T2, 312T3, . . . at the respective imaging times or an initial region of interest 313. The reference regions 312T1, 312T2, 312T3, . . . at the respective imaging times or the initial region of interest 312 can be made to overlap the fluorescent images 310T1, 310T2, 310T3, . . . , respectively, when the display image signal generation unit 54 generates a display image signal. In addition, a graph 320 showing a temporal change in the temporal fluorescence intensity ratio may be displayed. Such additional information can support more visually the determination of the change in the size of a lesion, such as cancer, or the temporal change in the content of NADH.

Figure 18:
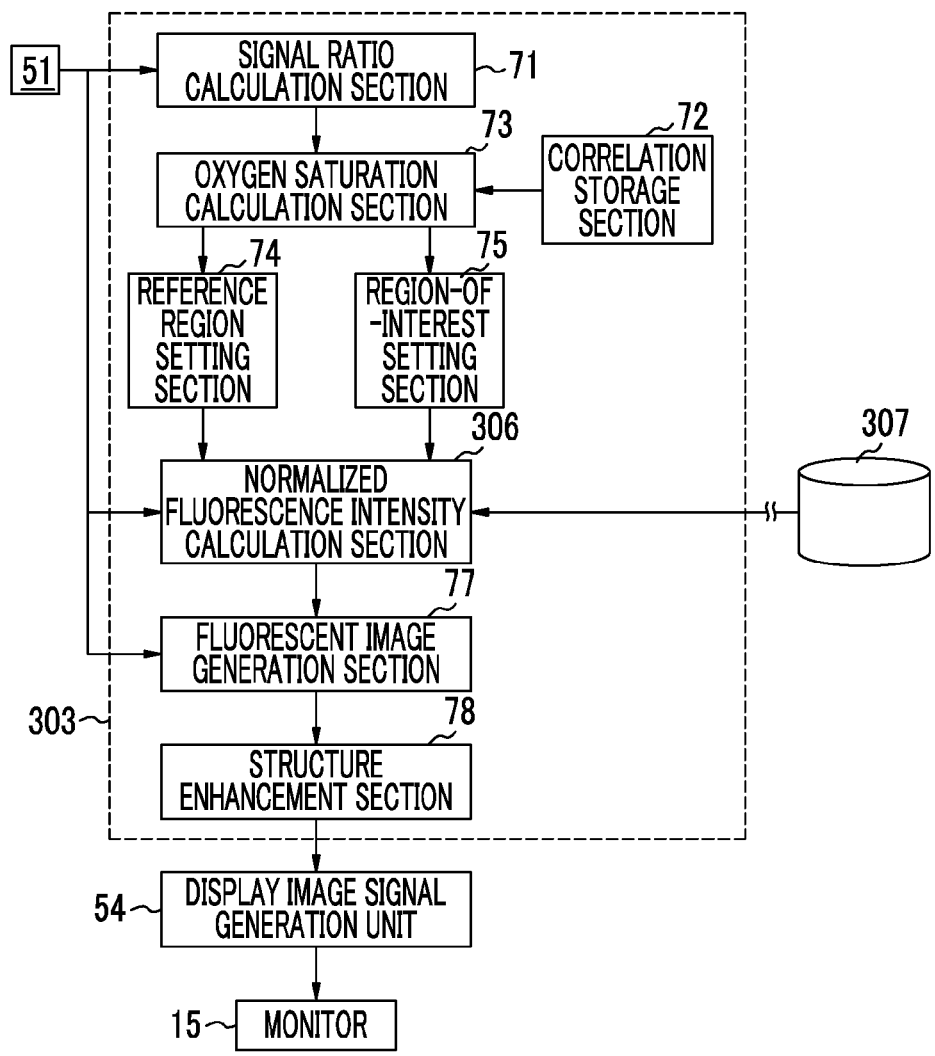
FIG. 18 is a block diagram in a modification example.

In the case of using the special observation image processing unit 303, temporal information is displayed as described above. However, the temporal information can be sequentially displayed in approximately real time during a single observation (inspection). It is also possible to display the temporal information using the results (image signals used for the generation of the past fluorescent images, setting of the reference region, setting of the region of interest, and the like) of the observation in the past, such as one week before or one month before. In the case of displaying the temporal information based on the past observation result, it is preferable to provide a database 307 in which past observation results are stored, as shown in FIG. 18. Then, the normalized fluorescence intensity calculation section 306 acquires the past observation result from the database 307, and calculates a temporal normalized fluorescence intensity based on the acquired past observation result. The database 307 may be provided outside the fluorescence observation device 10, or may be provided in the fluorescence observation device 10. In a case in which the database 307 is provided in the fluorescence observation device 10, the normalized fluorescence intensity calculation section 306 may store the past observation result so as to function as the database 307.

Fourth Embodiment

In the first to third embodiments, the reference region is set based on the oxygen saturation of the subject 11. However, the reference region may be set using another method. For example, a colorant may be administered to the subject 11, and the reference region may be set according to the colored color.

Figure 19:
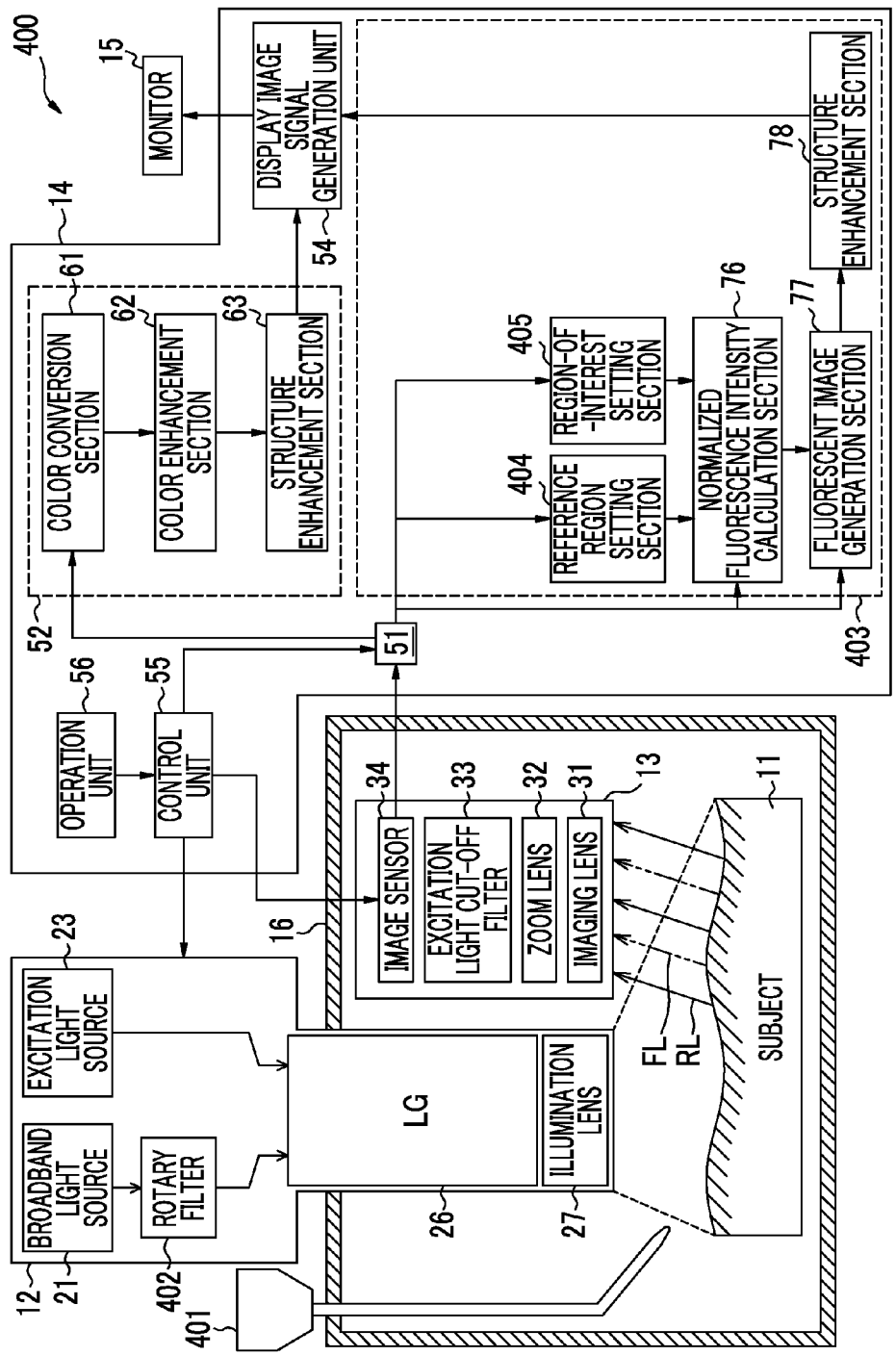
FIG. 19 is a block diagram of a fluorescence observation device of a fourth embodiment.
Figure 20:
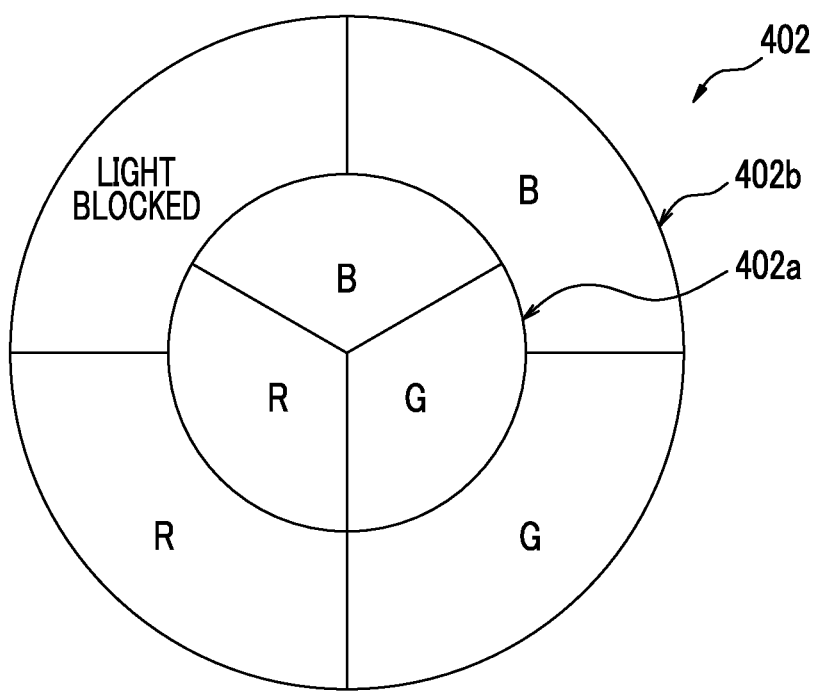
FIG. 20 is an explanatory diagram showing a rotary filter used in the fourth embodiment.

As shown in FIG. 19, a fluorescence observation device 400 includes a colorant administration unit 401 for administrating colorant to the subject 11. As shown in FIG. 20, a rotary filter 402 used in the fluorescence observation device 400 includes a normal observation filter 402a and a special observation filter 402b. The normal observation filter 402a is configured to include filters of the respective colors of B, G, and R, and the special observation filter 402b is configured to include filters of the respective colors of B, G, and R and a light shielding part. In addition, in the fluorescence observation device 400, the special observation image processing unit 53 of the first embodiment is replaced with a special observation image processing unit 403. The other configuration is the same as that of the fluorescence observation device 10 of the first embodiment.

In the special observation image processing unit 403, each section (the signal ratio calculation section 71, the correlation storage section 72, and the oxygen saturation calculation section 73) for calculating the oxygen saturation is not provided, and a reference region setting section 404 and a region-of-interest setting section 405 having different functions from the first embodiment are provided. The normalized fluorescence intensity calculation section 76, the fluorescent image generation section 77, and the structure enhancement section 78 are the same as in the first embodiment.

The reference region setting section 404 acquires image signals of the respective colors of B, G, and R through the image processing switching unit 51. Then, using the image signals, a region that is colored in a specific color (or a region that is not colored with a colorant) is set as a reference region. Similarly, the region-of-interest setting section 405 acquires image signals of the respective colors of B, G, and R through the image processing switching unit 51, and sets a region colored in a different specific color (or a region that is not colored with a colorant) from the reference region as a region of interest using the image signals.

Figure 21:
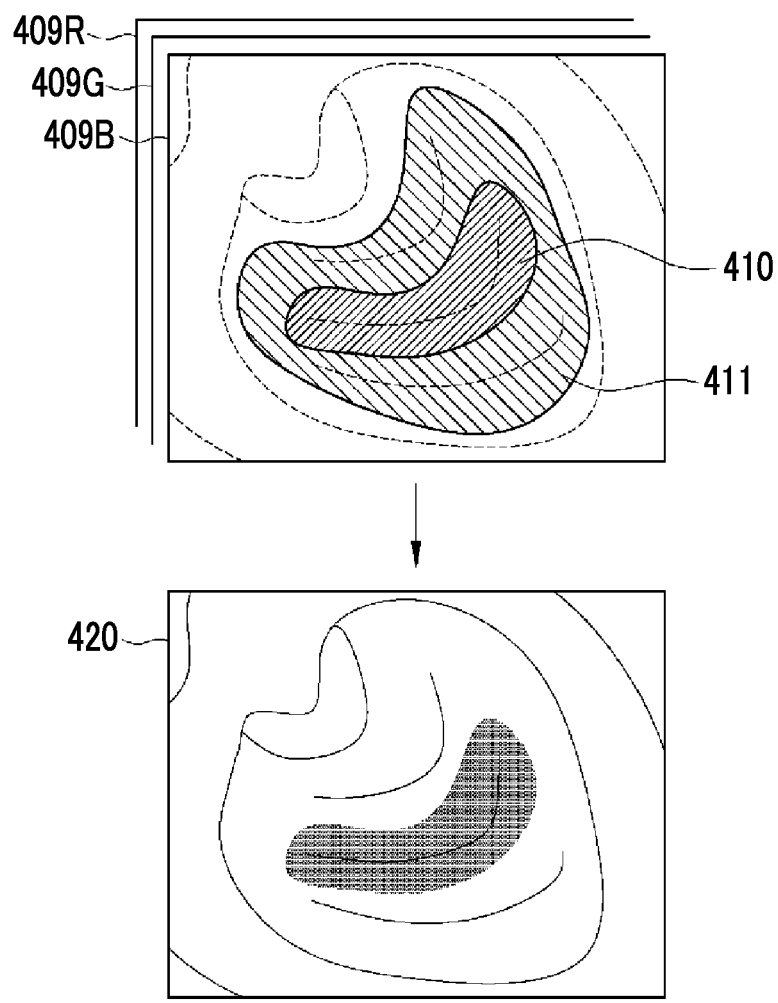
FIG. 21 is an explanatory diagram showing the operation in the fourth embodiment.

As shown in FIG. 21, in a case in which a pH indicator is administered to the subject 11 as a colorant, the region-of-interest setting section 405 extracts an acid region 410 where the pH is equal to or less than a specific value, from any of image signals 409R, 409G, and 409B of the respective colors or from a combination thereof, based on the color due to the pH indicator, and sets the acid region 410 as a region of interest. In addition, the reference region setting section 404 extracts a neutral region (or an alkaline region) 411 where the pH is equal to or greater than the specific value based on the color due to the pH indicator, and sets the neutral region 411 as a reference region. In many cases, the surface of the cancer tissue is acidic. Accordingly, by using the pH indicator, it is possible to set the cancer tissue as a region of interest and set the normal tissue as a reference region.

After the setting of the reference region or the region of interest is completed as described above, subsequent processing is performed as in the first embodiment. That is, also in the fluorescence observation device 400, it is possible to generate and display a fluorescent image 420 by pseudo-coloring the region of interest based on the normalized fluorescence intensity.

As colorants, it is possible to use not only the pH indicator but also indigo carmine, toluidine blue, methylene blue, Lugol's solution, crystal violet, fluorescein, acridine orange, indocyanine green, or acetic acid. In addition, these colorants including the pH indicator may be used in combination.

In addition, the configuration of the light source unit 12 of the fluorescence observation device 400 is arbitrary if illumination light by which the color due to a colorant can be identified and excitation light for emitting the fluorescence FL can be emitted to the subject 11 at least a part of which is colored with a colorant.

Although the fluorescence observation device 400 sets the reference region and the region of interest automatically, the fluorescence observation device 400 may be configured to be able to set these manually. In this case, a color image in which the color due to the colorant can be identified is generated and displayed, so that the user designates a reference region and a region of interest using the operation unit 56 by observing the coloring of the subject 11 by the colorant.

In addition, the control unit 55 of the fluorescence observation device 400 preferably performs imaging control so that the subject is imaged by emitting excitation light before the subject 11 is colored by the colorant, the fluorescent image signal $S_{FL}$ is output from the image sensor 34, and image signals of the corresponding respective colors are output by emitting illumination light beams of the respective colors of R, G, and B after the colorant is administered to the subject 11. In this manner, even if the color of the colorant and the wavelength band of the fluorescence FL overlap (or partially overlap) each other, the fluorescence observation of the subject 11 can be performed without being interfered by the color of the colorant.

In addition, the second and third embodiments can also be combined with the fluorescence observation device 400 of the fourth embodiment.

Fifth Embodiment

Figure 22:
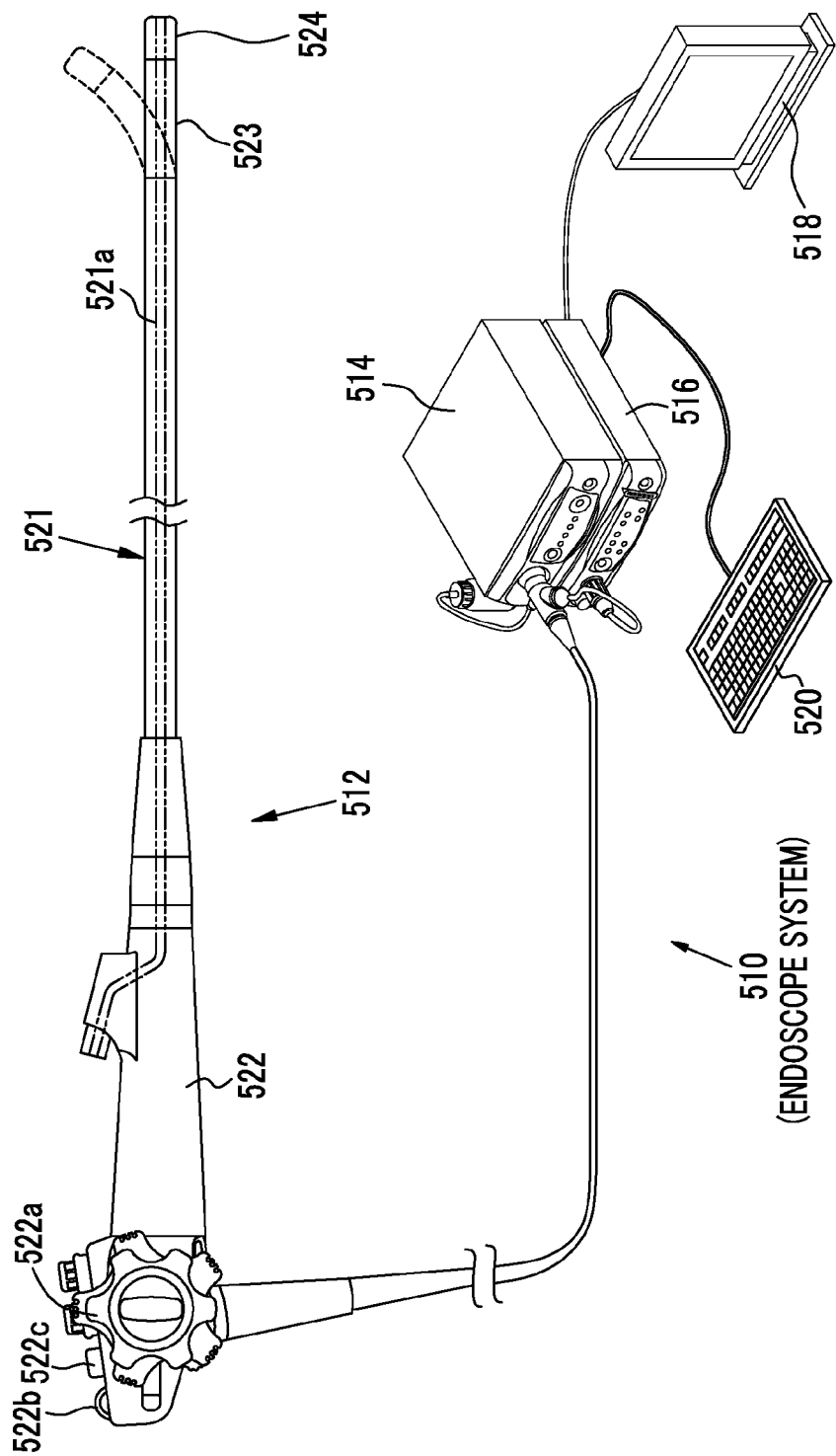
FIG. 22 is an external view of an endoscopic system.

The configuration of the fluorescence observation devices of each of the first to fourth embodiments can be mounted in an endoscopic system. As shown in FIG. 22, an endoscopic system 510 includes an endoscope 512, a light source device 514, a processor device 516, a monitor 518, and a console 520.

The endoscope 512 is optically connected to the light source device 514, and is electrically connected to the processor device 516. The endoscope 512 includes an insertion part 521 that is inserted into the subject, an operation unit 522 provided at the proximal end of the insertion part 521, and a bending portion 523 and a distal portion 524 that are provided on the distal side of the insertion part 521. By operating an angle knob 522a of the operation unit 522, the bending portion 523 is bent. The distal portion 524 can be directed in a desired direction by the bending operation. A forceps channel 521a for inserting a treatment instrument, such as forceps, therethrough is provided in the insertion part 521.

In addition to the angle knob 522a, a mode selector SW (mode selector switch) 522b and a zoom operation unit 522c are provided in the operation unit 522. The mode selector SW 522b is used for a switching operation between two modes of the normal observation mode and the special observation mode.

The processor device 516 is electrically connected to the monitor 518 and the console 520. The monitor 518 displays a normal observation image or a fluorescent image and information regarding the images (hereinafter, referred to as image information or the like). The console 520 functions as a user interface (UI) for receiving an input operation, such as a function setting. A recording unit (not shown) in which image information or the like is recorded may be connected to the processor device 516.

Figure 23:
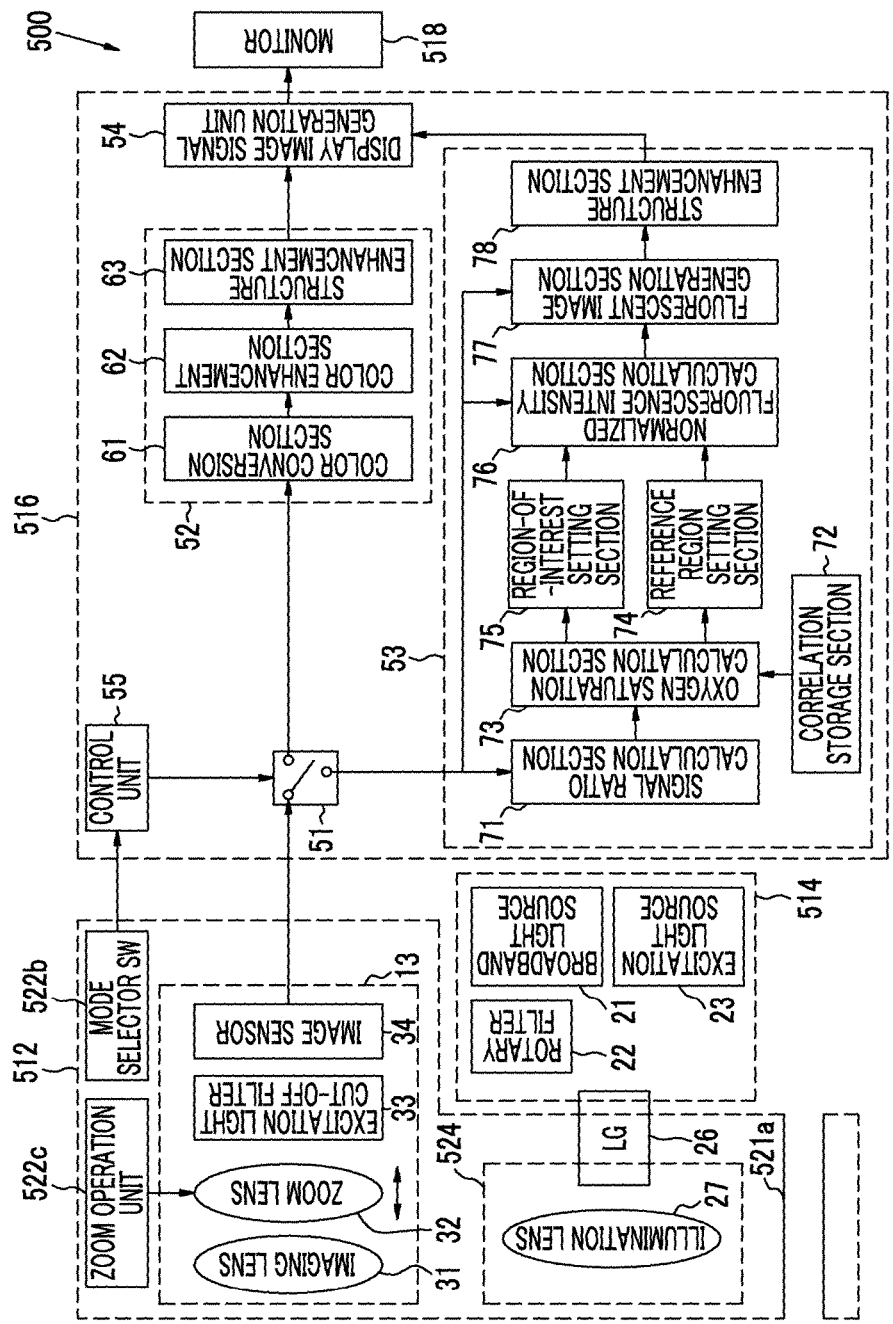
FIG. 23 is a block diagram of an endoscopic system corresponding to the fluorescence observation device of the first embodiment.
Figure 24:
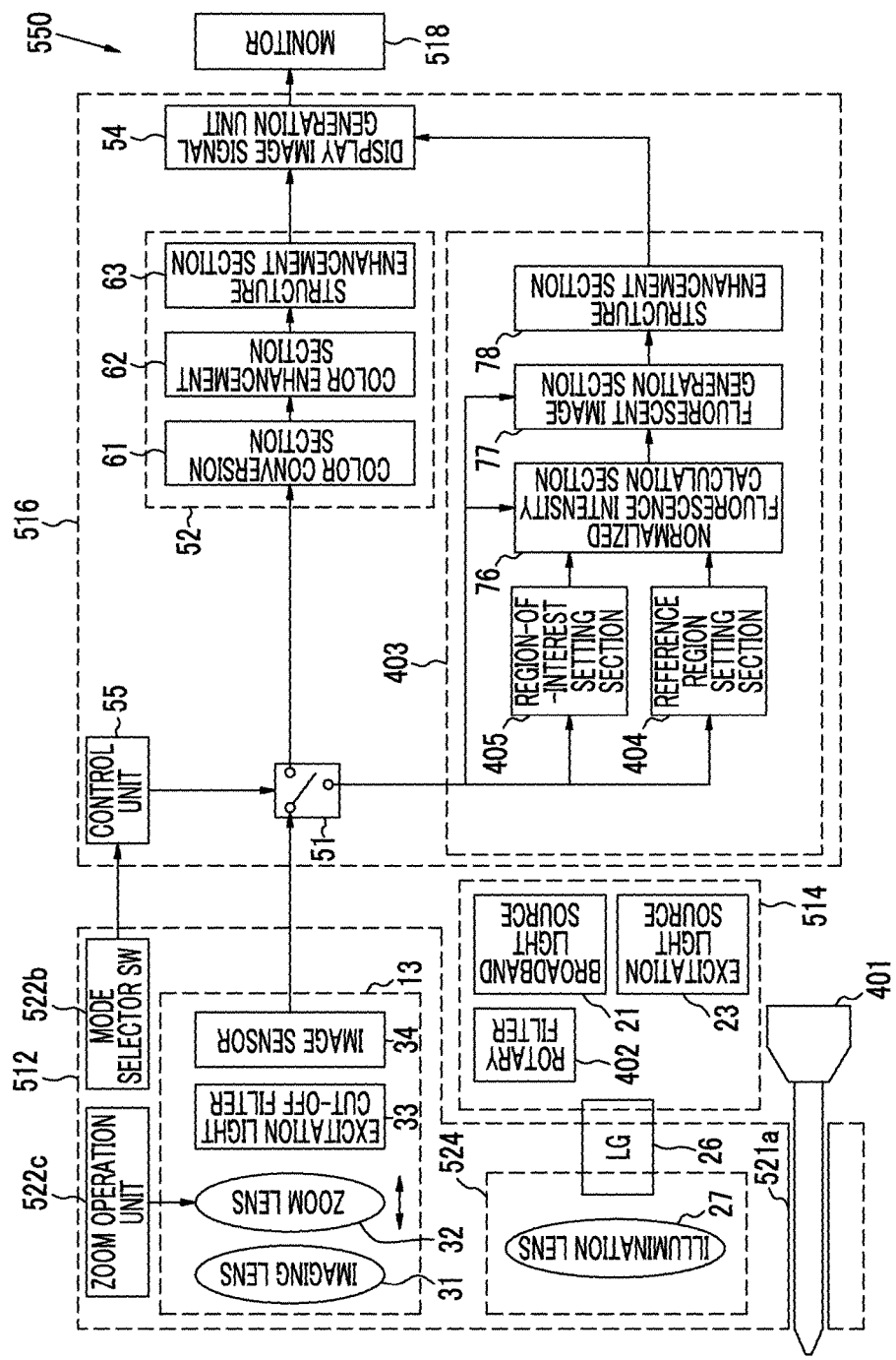
FIG. 24 is a block diagram of an endoscopic system corresponding to the fluorescence observation device of the fourth embodiment.

As shown in FIG. 23, the light source unit 12 of the fluorescence observation device 10 of the first embodiment can be provided in the light source device 514 and the distal portion 524. In addition, the imaging unit 13 can be provided in the endoscope 512, and each unit of the processor unit 14 can be provided in the processor device 516. As in an endoscopic system 550 shown in FIG. 24, each unit of the fluorescence observation device 400 of the fourth embodiment is also the same. In this case, a colorant administration unit 401 is a treatment instrument that is used in a state of being inserted into the forceps channel.

EXPLANATION OF REFERENCES 10, 400: fluorescence observation device
11: subject
12: light source unit
13: imaging unit
14: processor unit
15: monitor
16: dark box
21: broadband light source
22: rotary filter
23: excitation light source
33: excitation light cut-off filter
34: image sensor
52: normal observation image processing unit
53: special observation image processing unit
54: display image signal generation unit
71: signal ratio calculation section
73: oxygen saturation calculation section
74: reference region setting section
75: region-of-interest setting section
76: normalized fluorescence intensity calculation section
77: fluorescent image generation section
500, 550: endoscopic system

What is claimed is:

1. A fluorescence observation device, comprising:
a signal light source that irradiates a subject with signal light having a wavelength band where an absorption coefficient changes with an oxygen saturation of blood hemoglobin;
an excitation light source that irradiates the subject with excitation light for emitting fluorescence by exciting a fluorescent material contained in the subject;
an image sensor that images the subject with the signal light and outputs a first image signal and that images the subject with the fluorescence and outputs a second image signal; and
a processor unit that
  calculates an oxygen saturation of the subject for each pixel based on the first image signal,
  sets a reference region of the subject based on the oxygen saturation,
  sets a region of interest of the subject,
  calculates a normalized fluorescence intensity indicating a normalized emission intensity of the fluorescence by dividing a region-of-interest fluorescence intensity, which is calculated using a pixel value of the region of interest of the subject in the second image signal, by a reference fluorescence intensity calculated using a pixel value of the reference region of the subject in the second image signal, and generates a fluorescent image of the region of interest which is pseudo colored based on the normalized fluorescence intensity.

2. The fluorescence observation device according to claim 1,
wherein the processor unit sets the region of interest based on the oxygen saturation.

3. The fluorescence observation device according to claim 2,
wherein the processor unit sets a region where the oxygen saturation falls within a specific range as the reference region.

4. The fluorescence observation device according to claim 2, further comprising:
a display unit that displays a fluorescent image,
wherein the processor unit obtains a plurality of fluorescent images by imaging the same subject at two or more different times, and
displays the plurality of fluorescent images in time series on the display unit.

5. The fluorescence observation device according to claim 1,
wherein the processor unit sets the region of interest based on shape information of the subject.

6. The fluorescence observation device according to claim 5,
wherein the processor unit sets a region where the oxygen saturation falls within a specific range as the reference region.

7. The fluorescence observation device according to claim 5, further comprising:
a display unit that displays a fluorescent image,
wherein the processor unit obtains a plurality of fluorescent images by imaging the same subject at two or more different times, and
displays the plurality of fluorescent images in time series on the display unit.

8. The fluorescence observation device according to claim 1,
wherein the processor unit sets a region where the oxygen saturation falls within a specific range as the reference region.

9. The fluorescence observation device according to claim 8, further comprising:
a display unit that displays a fluorescent image,
wherein the processor unit obtains a plurality of fluorescent images by imaging the same subject at two or more different times, and
displays the plurality of fluorescent images in time series on the display unit.

10. The fluorescence observation device according to claim 1, further comprising:
a display unit that displays a fluorescent image, wherein the processor unit obtains a plurality of fluorescent images by imaging the same subject at two or more different times, and
displays the plurality of fluorescent images in time series on the display unit.

11. The fluorescence observation device according to claim 1,
wherein the processor unit calculates the normalized fluorescence intensity using the region of interest set at a specific time of imaging and the reference region set at each time of imaging.

12. A fluorescence observation device, comprising:
an illumination light source that irradiates a subject, at least a part of which is colored with a colorant, with illumination light by which a color due to the colorant can be identified;
an excitation light source that irradiates the subject with excitation light for emitting fluorescence by exciting a fluorescent material contained in the subject;
an image sensor that images the subject with the illumination light and outputs a first image signal and that images the subject with the fluorescence and outputs a second image signal; and
a processor unit that
sets a reference region according to a color due to the colorant,
sets a region of interest of the subject,
calculates a normalized fluorescence intensity indicating a normalized emission intensity of the fluorescence by dividing a region-of-interest fluorescence intensity, which is calculated using a pixel value of the region of interest of the subject in the second image signal, by a reference fluorescence intensity calculated using a pixel value of the reference region of the subject in the second image signal, and
generates a fluorescent image of the region of interest which is pseudo colored based on the normalized fluorescence intensity.

13. The fluorescence observation device according to claim 12,
wherein the processor unit sets the region of interest according to a color due to the colorant.

14. The fluorescence observation device according to claim 12,
wherein the colorant is a pH indicator that changes with pH of the subject.

15. The fluorescence observation device according to claim 14,
wherein the processor unit sets a region where the pH is equal to or greater than a specific value as the reference region.

16. The fluorescence observation device according to claim 12,
wherein the colorant contains at least one of indigo carmine, toluidine blue, methylene blue, Lugol's solution, crystal violet, fluorescein, acridine orange, indocyanine green, or acetic acid.

17. The fluorescence observation device according to claim 12,
wherein the processor unit generates the fluorescent image of the region of interest which is pseudo-colored, by using the second image signal obtained from the subject with fluorescence before the colorant is administered to the subject and the first image signal obtained from the subject with the illumination light after the colorant is administered to the subject.

18. An endoscopic system, comprising:
a signal light source that irradiates a subject with signal light having a wavelength band where an absorption coefficient changes with an oxygen saturation of blood hemoglobin;
an excitation light source that irradiates the subject with excitation light for emitting fluorescence by exciting a fluorescent material contained in the subject;
an image sensor that images the subject with the signal light and outputs a first image signal and that images the subject with the fluorescence and outputs a second image signal; and processor unit that
  calculates an oxygen saturation of the subject for each pixel based on the first image signal,
  sets a reference region of the subject based on the oxygen saturation,
  sets a region of interest of the subject,
  calculates a normalized fluorescence intensity indicating a normalized emission intensity of the fluorescence by dividing a region-of-interest fluorescence intensity, which is calculated using a pixel value of the region of interest of the subject in the second image signal, by a reference fluorescence intensity calculated using a pixel value of the reference region of the subject in the second image signal, and
  generates a fluorescent image of the region of interest which is pseudo colored based on the normalized fluorescence intensity.

19. A processor device of an endoscopic system including a signal light source that irradiates a subject with signal light having a wavelength band where an absorption coefficient changes with an oxygen saturation of blood hemoglobin, an excitation light source that irradiates the subject with excitation light for emitting fluorescence by exciting a fluorescent material contained in the subject, and an image sensor that images the subject with the signal light and outputs a first image signal and that images the subject with the fluorescence and outputs a second image signal, the processor device comprising:
  a processor unit that
    calculates an oxygen saturation of the subject for each pixel based on the first image signal,
    sets a reference region of the subject based on the oxygen saturation,
    sets a region of interest of the subject,
    calculates a normalized fluorescence intensity indicating a normalized emission intensity of the fluorescence by dividing a region-of-interest fluorescence intensity, which is calculated using a pixel value of the region of interest of the subject in the second image signal, by a reference fluorescence intensity calculated using a pixel value of the reference region of the subject in the second image signal, and
    generates a fluorescent image of the region of interest which is pseudo colored based on the normalized fluorescence intensity.

20. An operation method of a device including a signal light source that irradiates a subject with signal light having a wavelength band where an absorption coefficient changes with an oxygen saturation of blood hemoglobin, an excitation light source that irradiates the subject with excitation light for emitting fluorescence by exciting a fluorescent material contained in the subject, and an image sensor that images the subject with the signal light and outputs a first image signal and that images the subject with the fluorescence and outputs a second image signal, the operation method comprising:
  an oxygen saturation calculation step of calculating an oxygen saturation of the subject for each pixel based on the first image signal;
  a reference region setting step of setting a reference region of the subject based on the oxygen saturation;
  a region-of-interest setting step of setting a region of interest of the subject;
  a normalized fluorescence intensity calculation step of calculating a normalized fluorescence intensity indicating a normalized emission intensity of the fluorescence by dividing a region-of-interest fluorescence intensity, which is calculated using a pixel value of the region of interest of the subject in the second image signal, by a reference fluorescence intensity calculated using a pixel value of the reference region of the subject in the second image signal; and
  a fluorescent image generation step of generating a fluorescent image of the region of interest which is pseudo colored based on the normalized fluorescence intensity.

* * * * *